US007467047B2

(12) United States Patent
Vaidyanathan et al.

(10) Patent No.: US 7,467,047 B2
(45) Date of Patent: Dec. 16, 2008

(54) METHOD OF DISCOVERING PATTERNS IN SYMBOL SEQUENCES

(75) Inventors: Akhileswar Ganesh Vaidyanathan, Hockessin, DE (US); David Reuben Argentar, Bear, DE (US); Karen Marie Bloch, Wilmington, DE (US); Herbert Alan Holyst, Morton, PA (US); Allan Robert Moser, Swarthmore, PA (US); Wade Thomas Rogers, West Chester, PA (US)

(73) Assignee: E.I. Du Pont de Nemours & Company, Wilmington, DE (US)

( * ) Notice: Subject to any disclaimer, the term of this patent is extended or adjusted under 35 U.S.C. 154(b) by 63 days.

(21) Appl. No.: 09/851,674

(22) Filed: May 9, 2001

(65) Prior Publication Data

US 2003/0220771 A1    Nov. 27, 2003

Related U.S. Application Data

(60) Provisional application No. 60/203,440, filed on May 10, 2000.

(51) Int. Cl.
*G01N 33/48* (2006.01)
(52) U.S. Cl. .......................................... 702/20; 702/19
(58) Field of Classification Search .................. 702/20, 702/19; 703/11; 435/6
See application file for complete search history.

(56) References Cited

U.S. PATENT DOCUMENTS

| | | | |
|---|---|---|---|
| 5,577,249 A * | 11/1996 | Califano | 707/100 |
| 5,977,890 A | 11/1999 | Rigoutsos et al. | |
| 6,092,065 A | 7/2000 | Floratos et al. | |
| 6,108,666 A | 8/2000 | Floratos et al. | |

FOREIGN PATENT DOCUMENTS

| EP | 0898236 A2 | 1/2001 |
|---|---|---|
| EP | 0898236 A3 | 1/2001 |
| WO | WO00/26818 | 5/2000 |
| WO | WO00/26819 | 5/2000 |

OTHER PUBLICATIONS

Merriam-Webster Online, www.m-w.com/cgi-bin/dictionary?/book=Dictionary&va=collecting, last visited Dec. 12, 2005.*
Finding flexible patterns in unaligned protein sequences. Inge Jonassen, John Collins and Desmond G. Higgins. Protein Science (1995) 4:1587-1595. Cambridge University Press.
SPLASH: structural pattern localization analysis by sequential histograms. Andrea Califano. Bioinformatics, vol. 16, No. 4, 2000. pp. 341-357.
Combinatorial pattern discovery in biological sequences: The Teiresias algorithm. Isidore Rigoutsos and Aris Floratos. Bioinformatics, vol. 14. No. 1, 1998. pp. 55-67.
Tarhio, Jorma and Esko Ukkonen. Approximate Boyer-Moore String Matching. 1993 Society for Industrial and Applied Mathematics. vol. 22, No. 2m oo, 243-260, Apr. 1993.

* cited by examiner

Primary Examiner—John S. Brusca
Assistant Examiner—Jerry Lin
(74) Attorney, Agent, or Firm—George M. Medwick

(57) ABSTRACT

A method of discovering one or more patterns in two sequences of symbols $S_1$ and $S_2$ includes the formation, for each sequence, of a master offset table that groups for each symbol the position in the sequence occupied by each occurrence of that symbol. The difference in position between each occurrence of a symbol in one of the sequences and each occurrence of that same symbol in the other sequence is determined and a Pattern Map is formed. For each given value of a difference in position the Pattern Map lists the position in the first sequence of each symbol therein that appears in the second sequence at that difference in position. The collection of the symbols tabulated for each value of difference in position thereby defines a parent pattern in the first sequence that is repeated in the second sequence.

A computer readable medium having instructions for controlling a computer system to perform the method and a computer readable medium containing a data structure used in the practice of the method are also disclosed.

22 Claims, 14 Drawing Sheets

S1 MOT Table

| A | C | D | E | F | G | H | I | K | L | M | N | P | Q | R | S | T | V | W | Y |
|---|---|---|---|---|---|---|---|---|---|---|---|---|---|---|---|---|---|---|---|
| 5 | 1 | 8 | 0 | 6 | 2 | 3 | 33 | 20 | 18 |   | 16 | 17 | 10 | 44 | 7 | 23 | 12 | 11 | 9 |
| 36 | 41 | 13 | 15 | 28 | 31 | 4 | 37 | 25 | 46 |   |   | 22 | 19 |   | 24 | 29 | 21 |   |   |
|   |   | 14 |   | 42 |   | 40 |   | 34 |   |   |   | 26 | 43 |   | 45 |   | 30 |   |   |
|   |   | 32 |   |   |   |   |   | 35 |   |   |   | 27 |   |   |   |   |   |   |   |
|   |   |   |   |   |   |   |   |   |   |   |   | 38 |   |   |   |   |   |   |   |
|   |   |   |   |   |   |   |   |   |   |   |   | 39 |   |   |   |   |   |   |   |

S2 MOT Table

| A | C | D | E | F | G | H | I | K | L | M | N | P | Q | R | S | T | V | W | Y |
|---|---|---|---|---|---|---|---|---|---|---|---|---|---|---|---|---|---|---|---|
| 33 | 0 |   | 1 | 19 | 3 | 28 | 17 | 8 | 6 |   | 52 | 11 | 20 | 7 | 13 | 26 | 2 | 34 | 38 |
| 40 | 36 |   | 39 | 47 | 41 | 42 |   | 10 | 23 |   |   | 16 | 44 | 21 | 22 |   | 4 | 46 | 45 |
|   |   |   |   |   | 49 | 43 |   | 14 | 30 |   |   | 25 |   | 31 |   |   | 5 | 50 | 48 |
|   |   |   |   |   | 53 |   |   | 32 |   |   |   | 27 |   |   |   |   | 9 |   |   |
|   |   |   |   |   |   |   |   |   |   |   |   |   |   |   |   |   | 12 |   |   |
|   |   |   |   |   |   |   |   |   |   |   |   |   |   |   |   |   | 15 |   |   |
|   |   |   |   |   |   |   |   |   |   |   |   |   |   |   |   |   | 18 |   |   |
|   |   |   |   |   |   |   |   |   |   |   |   |   |   |   |   |   | 24 |   |   |
|   |   |   |   |   |   |   |   |   |   |   |   |   |   |   |   |   | 29 |   |   |
|   |   |   |   |   |   |   |   |   |   |   |   |   |   |   |   |   | 35 |   |   |
|   |   |   |   |   |   |   |   |   |   |   |   |   |   |   |   |   | 37 |   |   |
|   |   |   |   |   |   |   |   |   |   |   |   |   |   |   |   |   | 51 |   |   |

METHOD OF DISCOVERING PATTERNS IN SYMBOL SEQUENCES

CROSS REFERENCE TO RELATED APPLICATION

This application claims benefit of priority from Provisional application Ser. No. 60/203,440, filed on May 10, 2000.

FIELD OF THE INVENTION

The present invention relates to a computationally efficient method of finding patterns in sequences of symbols written in a particular alphabet, to a computer readable medium having instructions for controlling a computer system to perform the method, and to a computer readable medium containing a data structure used in the practice of the method.

BACKGROUND OF THE INVENTION

Pattern Discovery is a nascent competency in the rapidly developing field of computational biology. As genomic data is collected at ever increasing rates it is essential that powerful tools be available to discover the key information embedded in sequence data. This information could be, for example, important sequence similarities across different genes, or structural relationships between similar proteins. Discovery of such information will facilitate biochemical discovery and will accelerate rapid development of new products engineered to have desired end use properties.

Computational biology is defined as "A field of biology concerned with the development of techniques for the collection and manipulation of biological data, and the use of such data to make biological discoveries or predictions. This field encompasses all computational methods and theories applicable to molecular biology and areas of computer-based techniques for solving biological problems including manipulation of models and datasets" (Online Medical Dictionary, 1998, 1999).

Sequence analysis is a central subset of the very broad area of computational biology. Sequence analysis, as it pertains to the determination of the amount and nature of sequence similarity, or homology, is especially important. Pattern discovery is an important part of sequence analysis.

There are numerous methods commonly used to search for and understand various forms of sequence homology. Among these are single- and multiple-sequence alignment (e.g. CLUSTAL) and sequence matching (e.g. BLAST) algorithms. Although these methods are extremely useful, they have limitations. In particular, there are many problems that seem to be characterized by low or undetectable homology at the sequence level, despite evidence of structural or functional similarity. Unfortunately, alignment-based methods tend to work best in the high-homology limit, and less well as homology decreases.

In view of the foregoing it is believed advantageous to be able to discover both pure and corrupted patterns within a given sequence and also between a family of sequences, regardless of homology.

SUMMARY OF THE INVENTION

In one aspect the present invention is directed to a method of discovering one or more patterns in two sequences of symbols $S_1$ and $S_2$, where the symbols are members of an alphabet.

In accordance with the method, for each sequence, a master offset table is formed. The master offset table groups for each symbol the position (position index) in the sequence occupied by each occurrence of that symbol. The difference in position between each occurrence of a symbol in one of the sequences and each occurrence of that same symbol in the other sequence is determined. A Pattern Map, typically in the form of a table, is formed. Each row in the table represents a single value of "difference in position". For each given value of a difference in position, the table lists the position in the first sequence of each symbol in the first sequence that appears in the second sequence with that difference in position. The collection of the symbols tabulated for each value of difference in position thereby defines a parent pattern in the first sequence that is repeated in the second sequence.

The Pattern Map may also list the number of symbols tabulated for each value of a difference in position. Thus, those parent patterns in the Pattern Map that have a number of symbols greater than a predetermined threshold may be readily identified from the number of symbols tabulation.

In a more detailed embodiment the invention pertains to a method of discovering one or more patterns in two sequences of symbols, the symbols being members of an alphabet, the first sequence of symbols having a length L1 and the second sequence of symbols having a length L2, comprising the steps of: a) translating the sequences of symbols into a table of ordered (symbol, position index) pairs, where the position index of each (symbol, position index) pair refers to the location of the symbol in a sequence; b) for each of the two sequences, grouping the (symbol, position index) pairs by symbol to respectively form a first master offset table and a second master offset table; c) forming a Pattern Map comprising an array having (L1+L2−1) rows by: i) subtracting the position index of the first master offset table from the position index of the second master offset table for every combination of (symbol, position index) pair having like symbols, the difference resulting from each subtraction defining a row index; ii) repeatedly storing each (symbol, position index) pair from the first master offset table in a row of the Pattern Map, the row being defined by the row index, until all (symbol, position index) pairs have been stored in the Pattern Map; d) defining a parent pattern by populating an output array with the symbols of each (symbol, position index) pair of a row of the Pattern Map, the symbols being placed at relative locations in the parent pattern indicated by the position index of the pair; and e) repeating step d) for each row of the Pattern Map.

In another aspect the invention is directed to a computer-readable medium containing instructions for controlling a computer system to discover one or more patterns in two sequences of symbols $S_1$ and $S_2$ by performing the method steps described above.

In still another aspect the invention is directed to a computer-readable medium containing a data structure useful by a computer system in the practice of the method steps described above.

BRIEF DESCRIPTION OF THE FIGURES

The invention will be more fully understood from the following detailed description, taken in connection with the accompanying drawings, which form a part of this application and in which:

FIG. 1 depicts master offset tables ("MOT tables") for sequences $S_1$ and $S_2$ of the first example;

FIGS. 2A and 2B show the Pattern Map of the first example;

FIGS. 7A and 7B illustrate an example of the formation of "tuples" in accordance with the method of the present invention;

DETAILED DESCRIPTION OF THE INVENTION

Figure 3:
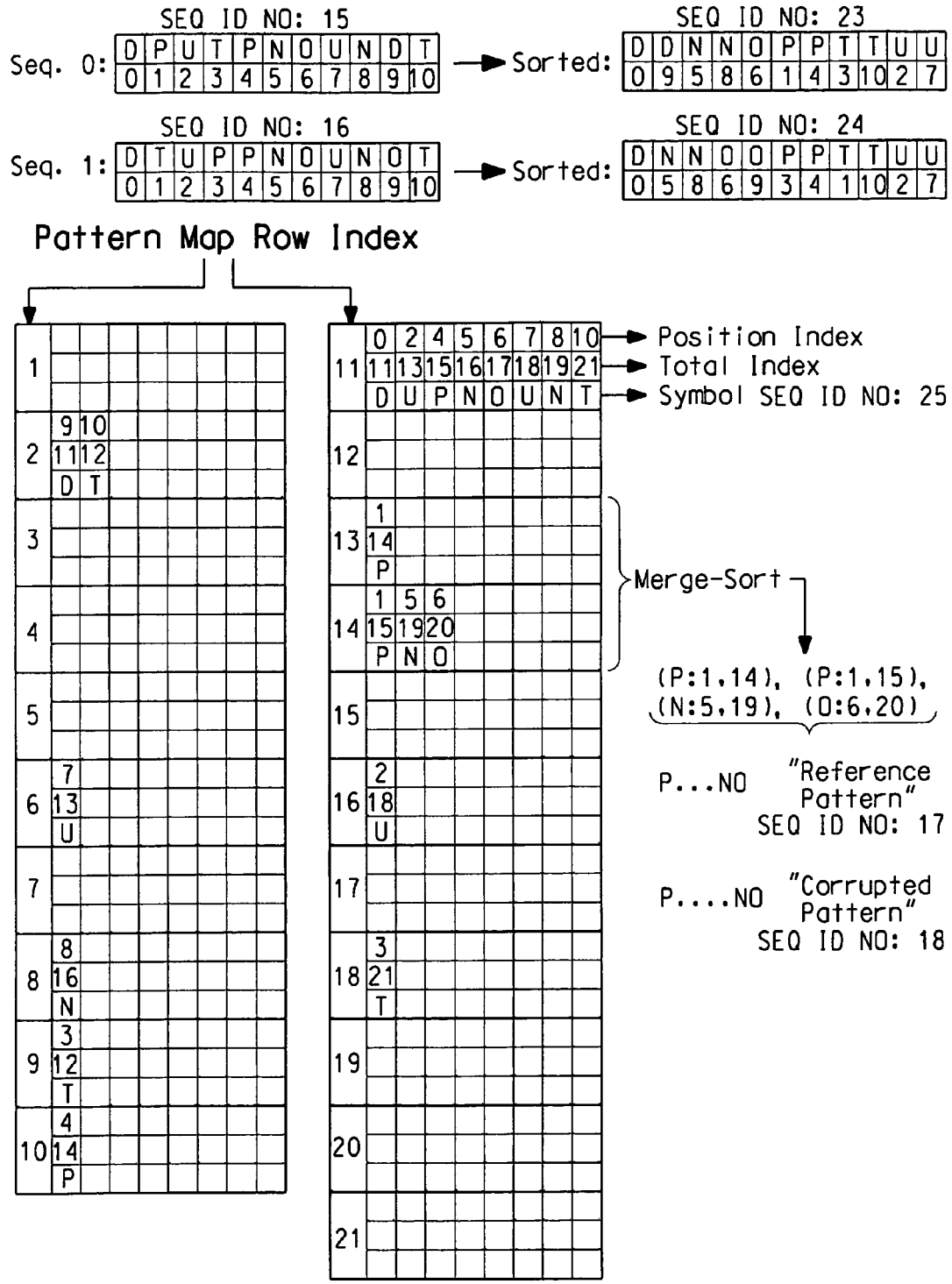
FIG. 3 shows a second example showing the discovery of corrupted patterns.

Throughout the following detailed description, similar reference numerals refer to similar elements in all figures of the drawings.

The present invention is independent of the particular alphabet in which sequences are represented. In fact, a useful preliminary step is to discover all of the symbols in the alphabet in which the sequence data are written. The term "alphabet" is meant to include any collection of letters or other characters (including numerals). For example, sequences describing DNA are typically written in a four-symbol alphabet consisting of the symbols {A,G,C,T}. Protein sequences are written in a twenty-symbol alphabet representing the amino acids, consisting of the symbols {A,C,D,E,F,G,H,I,K,L,M,N,P,Q,R,S,T,V,W,Y}.

Sometimes it is advantageous to transform the original representation of the sequence data into some alternate alphabet using some mapping function. The number of symbols in such a derived alphabet may be less than, equal to, or greater than the number of symbols in the original alphabet. However, the information content in the transformed representation may be different, allowing for the discovery of different (and perhaps more useful) features in the data.

An approach to mapping that reduces the number of symbols in the alphabet is an amino acid to physico-chemical-property mapping. In this case, amino acids are clustered into groups of relatively similar chemical or physical properties. For example, one might divide up the amino acids into groups called "aromatic", "acidic", "basic", "polar", "hydrophobic", and "other". These groups might each be represented by a respective symbol, for example {r, a, b, p, h, o}. Each of the twenty amino acid symbols is placed into one and only one of these groups. Thus, rewriting the sequences according to this mapping will yield sequences of exactly the same lengths, i.e., the same number of symbols, as the original sequences, but written in an alphabet of six symbols rather than the original twenty symbols. Applying the pattern discovery method of the present invention to these transformed sequences will produce patterns whose symbols represent amino acids of similar physico-chemical properties rather than patterns representing amino acid identity. This can be useful, for example, for discovering features in proteins that depend on one or more gross properties and that are insensitive to substitutions within a given property family.

An approach to mapping that increases the number of symbols in the alphabet is a mapping that forms combinations of symbols in the input alphabet. In such an implementation pairs (or triples, quadruples, and so forth) of symbols can be mapped to a single output symbol. For example, suppose the input sequence begins with "ACDF..." (SEQ ID NO:1). The first two symbols "AC" could map to the output symbol "a". The next pair of symbols "CD" might map to the output symbol "b". The symbols "DF" might map to "c", and so forth. In this specific example groups of n adjacent symbols are mapped to one output symbol. The output sequence will be shortened by (n-1) symbols due to end effects, but the number of possible symbols in the output alphabet is increased. If there are twenty symbols in the input alphabet, then there are a possible $20^n$ symbols in the output alphabet. Thus, taking n=2, there are a possible four hundred symbols in the output alphabet. With n=3, there would be eight thousand possible symbols in the output alphabet.

It will be appreciated that combining these two approaches an output alphabet may be produced that has a size that is less than, equal to, or greater than the size of the original alphabet.

The basic implementation of the method of the present invention may be understood by considering the forty-seven place sequence $S_1$ and the fifty-four place sequence $S_2$:

$S_1$:
ECGHHAFSDYQWVDDENPLQKVPTSKPPFT VGDIKKAIPPHCFQRSL (SEQ ID NO:2)

$S_2$:
CEVGVVLRKVKPVSKVPIVFQRSLVPT PHVLRKAWVCVYEAGHHQYWFYGWVNG (SEQ ID NO:3)

A "pattern" is defined as any distributed substring that occurs in at least two sequences in a set of sequences S ={$S_1$, $S_2$,...,$S_n$}. A distributed substring may comprise any selected symbols from a sequence, possibly separated by gaps.

The pattern L.KV... V... PH (SEQ ID NO:4) is found in both sequences (shown underlined in the above statement of the sequences $S_1$ and $S_2$). Here, the dots represent locations where the symbols in the two sequences do not match, and are thus considered placeholder positions in the pattern.

The term "occurs" in the definition of a pattern does not necessarily imply exactness. That is, in order for a pattern to occur in a sequence, it is possible to find that its occurrence is only approximate, having been corrupted in some way. Certain types of corruption, including slight misplacement of the pattern's symbols in the sequence (due to insertions or deletions, discussed in more detail below), or the possible substitution of a symbol for another, may be tolerated. Therefore, the present invention is useful for both pure pattern discovery (that is, the discovery of patterns which occur identically in at least two sequences) and corrupted pattern discovery (wherein patterns are discovered which occur approximately in at least two sequences, but not necessarily exactly).

The MOT Table Data Structure

The method of the present invention is based upon the translation of a sequence written as a list of symbols into a position-based data structure that groups, for each symbol in the sequence, the position in the sequence occupied by each occurrence of that symbol. The position of each symbol in the sequence is identified by its "position index". The "position index" is the number of places from the beginning of the sequence occupied by the symbol. This position-based data structure is called the "Master Offset Table", also referred to as a "MOT table".

The MOT tables for $S_1$ and $S_2$ are as shown in FIG. 1. Each MOT table has a column corresponding to each symbol in the alphabet. Each column stores, as elements therein, the location (by position index) of every occurrence in the sequence of the symbol corresponding to that column. By convention, the first symbol in a sequence has index 0.

Thus, from the $S_1$ MOT table it may be observed that the symbol "F" occurs at the sixth, twenty-eighth and forty-second position indices in the first sequence. Similarly, from the $S_2$ MOT table it may be observed that the symbol "F" occurs at the nineteenth and forty-seventh position indices in the second sequence.

The Pattern Map Data Structure

For all of the symbols in one sequence the difference in position between each occurrence of a symbol in that sequence and each occurrence of that same symbol in the other sequence is determined. The "difference in position" between an occurrence of a symbol of interest in the first sequence and an occurrence of the same symbol in the second sequence is the sum of: (i) the number of places in the first sequence lying between the symbol of interest and the end of the first sequence; plus (ii) the number of places from the beginning of the second sequence until the occurrence of that symbol of interest in the second sequence.

Difference is position is believed most easily determined by constructing another data structure called the "Pattern Map". The Pattern Map is a table of difference-in-position values. In forming the Pattern Map only index differences from corresponding MOT columns are computed (A's from A's, C's from C's, etc.). By focusing on position differences the present invention avoids the computational cost of exhaustive symbol-by-symbol comparison of the two sequences. The value of each row number in the Pattern Map corresponds to a value of a difference in position of a corresponding number of places. Thus, row "15" of the Pattern Map lists symbols that have a difference-in-position value of fifteen, that is, that are fifteen places apart.

Figure 2A:
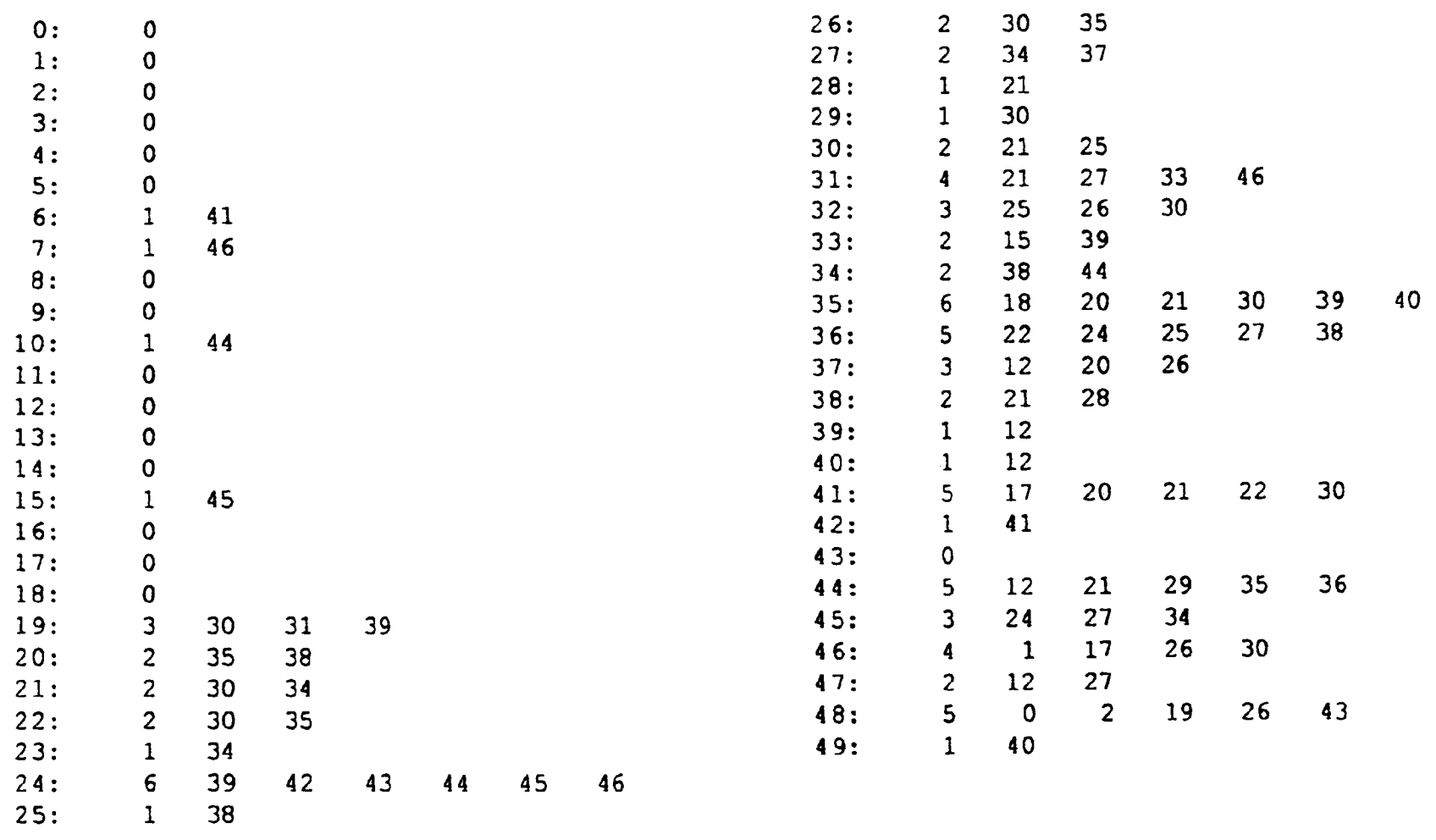
Figure 2B:
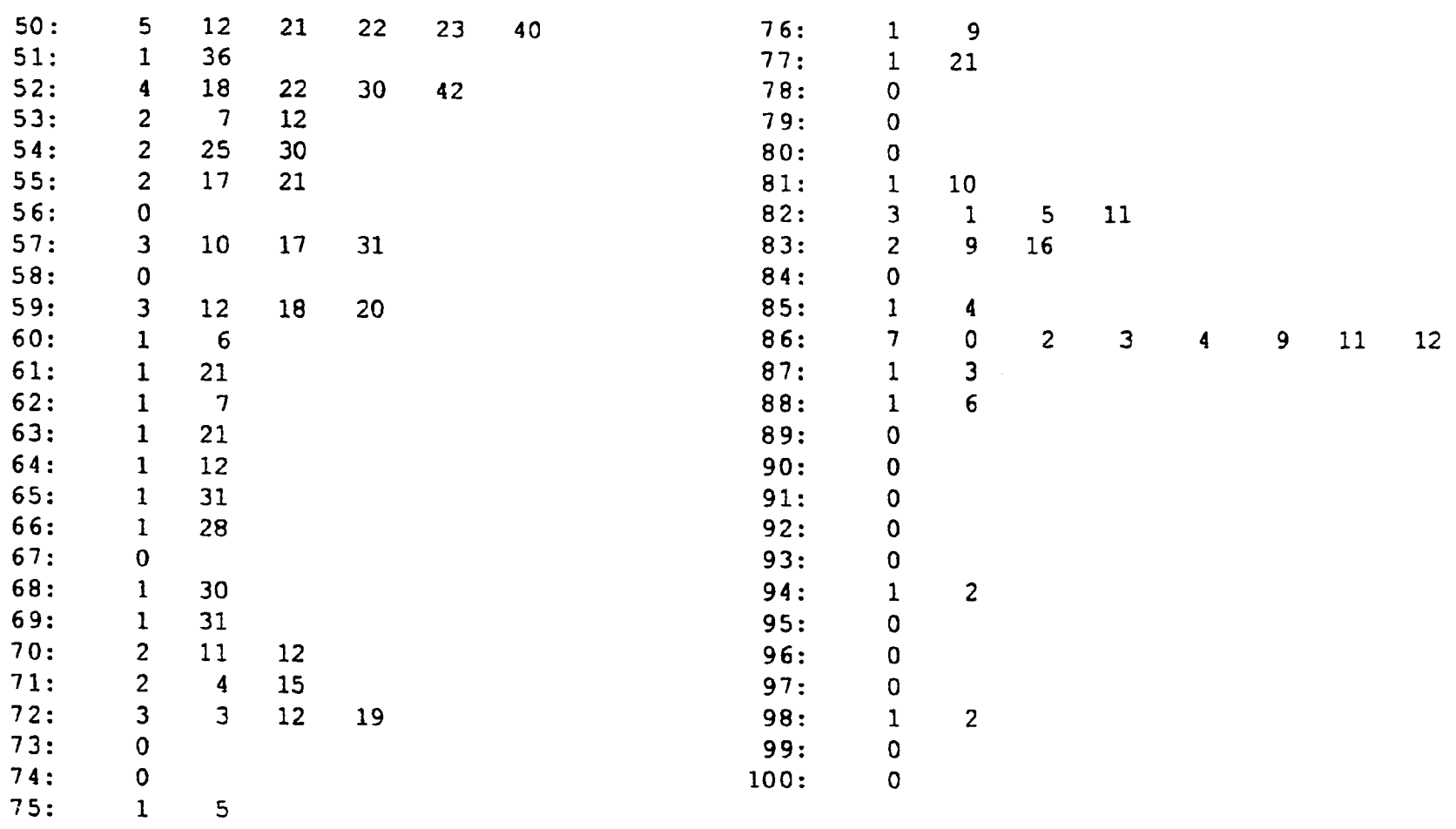

The value of a difference in position between a symbol in the first sequence and an occurrence of that same symbol in the other sequence may be determined in several ways. In a preferred implementation, in order to compute the Pattern Map, all of the indices in one MOT table (e.g., the MOT table corresponding to sequence $S_2$) are offset by the length of the other sequence (i.e., the sequence $S_1$). In effect, the sequence $S_2$ and the sequence $S_1$ are concatenated. It should be noted that the order of concatenation is immaterial. The following description describes a situation where sequence $S_2$ follows the sequence $S_1$. This offset is preferred because it results in non-negative indices in the Pattern Map. Then, for each element of each MOT table column, the index in $MOT_1$ is subtracted from the offset index of $MOT_2$. The result (i.e., the difference in position) is the row index of the Pattern Map, and the value stored in that row is the index from $MOT_1$ (again by convention). FIG. 2 shows the Pattern Map for sequences $S_1$, $S_2$ corresponding to the MOT tables of FIG. 1.

Alternatively, a signed difference between the position index of a symbol in a first sequence and the position index of that symbol in a second sequence may be determined. The length (number of places) of the first sequence is then added to the signed difference to produce the difference-in-position value. This alternative is computationally more intensive and is not preferred.

Referring to FIG. 2 the number to the left of the colon is the Pattern Map row index. The number to the immediate right of the colon is the symbol count in that row. The remaining numbers are indices from $MOT_1$.

The Pattern Map tabulates the symbols that have a given difference in position (that is, symbols that are that distance apart). The symbols are identified in the Pattern Map by their position index in the first sequence.

The Pattern Map sets forth, for each value of a difference in position, the position in the first sequence of each symbol therein that appears in the second sequence at that difference in position. Thus, for example, referring to the Pattern Map of FIG. 2, the "row index" numbered "10" sets forth the symbol(s) that are spaced apart by (that is, have a position difference value of) ten places. The number "44" appearing on that row of the Pattern Map refers to that symbol that appears in the second sequence at a distance of ten places from the position of that same symbol in the first sequence. The identity of the symbol is "R" which is the symbol that occupies the forty-fourth place in the sequence $S_1$. There is only one such symbol with a difference in position of ten places (hence the number "1" in the second column).

As another example the "row index" numbered "35" tabulates the six symbols that are spaced apart by (that is, have a position difference value of) thirty-five places. The numbers "18", "20", "21", "30", "39" and "40" appearing on that line of the table refers to those symbols that appear in the second sequence at a distance of thirty-five places from the appearance of that same symbol in the first sequence. By consulting $S_1$ it may be appreciated that:

position index "18" corresponds to symbol "L";
position index "20" corresponds to symbol "K";
position index "21" corresponds to symbol "V";
position index "30" corresponds to symbol "V";
position index "39" corresponds to symbol "P";
position index "40" corresponds to symbol "H".

As they appear in FIG. 2 the position indices in each row of the Pattern Map are sorted by increasing index value.

Reading out Patterns

Reading out patterns is now simple. The collection of the symbols tabulated for each value of difference in position (i.e., each row) in the Pattern Map defines a pattern in the first sequence that is repeated in the second sequence. Each row of the Pattern Map is a pattern of symbols contained in sequences $S_1$, $S_2$. The pattern, in symbolic form, is determined by consulting $S_1$ to determine the symbol at the location indicated by the Pattern Map index. For example, Pattern Map row 35 is the above-mentioned pattern L.KV...V...PH (SEQ ID NO:4). The pattern is constructed by noting the relative positions of these symbols and inserting the appropriate number of placeholders (one placeholder between the L and K, eight placeholders between the V and V, and eight placeholders between the V and P).

In practice a "MOT Column Index" may be stored along with the $MOT_1$ table entry, to facilitate pattern readout. The MOT Column Index indicates which MOT table column an index was derived from, and thereby what symbol it signifies. This avoids the necessity of consulting $S_1$ when reading out the pattern. This is a space-for-time computational tradeoff, where increased memory space is used to reduce the computational effort.

A pseudo-code program implementing the basic method of the present invention as described above, is as follows:

```
Begin;
{
    For all i in S
    {
        Build the MOT table MOT_i for S_i ;
    }
    For all unique pairs [S_i, S_j] in S
    {
        Compute the Pattern Map of [MOT_i, MOT_j] ;
        Select a minimum number of symbols for output patterns;
        Read out patterns from the Pattern Map
    }
}
End;
```

Very short patterns, i.e. patterns with only one, two or three symbols, may occur entirely by chance, especially in long sequences. Therefore, it is sometimes desirable to identify patterns from the Pattern Map that meet a predetermined selection criteria. This process is termed "filtering".

A first selection criteria is to identify patterns from the Pattern Map containing a number of symbols greater than a predetermined threshold number of symbols (e.g., four or more). Such patterns usually have an underlying causality. Since each row of the Pattern Map also sets forth the number of symbols that have the difference-in-position value corresponding to that row number, patterns that exceed the predetermined threshold may be found by a relatively straightforward comparison.

If, for example, it were desired to identify all those patterns that include more than four symbols, it may be seen by examination of the second column of the Pattern Map that there are eleven patterns of four or more symbols, thus:

| Pattern | | Row Index |
|---|---|---|
| P..FQRSL | (SEQ ID NO:5) | Line 24 |
| V......P.....I............L | (SEQ ID NO:6) | Line 31 |
| L.KV........V........PH | (SEQ ID NO:4) | Line 35 |
| P.SK.P..........P | (SEQ ID NO:7) | Line 36 |
| P..KVP.......V | (SEQ ID NO:8) | Line 41 |
| V.........V........T.....KA | (SEQ ID NO:9) | Line 44 |
| C................P........P...V | (SEQ ID NO:10) | Line 46 |
| E.G................Q......P..............Q | (SEQ ID NO:11) | Line 48 |
| V.........VPT................H | (SEQ ID NO:12) | Line 50 |
| L....P.......V............F | (SEQ ID NO:13) | Line 52 |
| E.GHH....Y.WV | (SEQ ID NO:14) | Line 86 |

The patterns within any sequence may be separate in the sense that the particular pattern begins and ends before another pattern in that sequence begins. Separate patterns may be contiguous to each other in that the first symbol of a second pattern may immediately after the last symbol of a first pattern. More commonly, however, the patterns in a sequence overlap each other, that is, one or more symbols of a second pattern may occur before the end of a first pattern. Patterns may also share one or more symbols.

A pseudo-code program implementing the basic method of the present invention and that further includes a filtering step is as follows:

```
Begin;
{
    For all i in S
    {
        Build the MOT table MOT_i for S_i ;
    }
    For all unique pairs [S_i, S_j] in S
    {
        Compute the Pattern Map of [MOT_i, MOT_j] ;
        Select a minimum number of symbols for output patterns;
        Read out patterns from the Pattern Map
            Determine patterns that meet minimum
            number of symbols requirement,
                ignoring the rest;
        Store in MOT table form for further processing;
        Cull duplicate patterns;
    }
}
End;
```

A second selection criteria that may be used to implement filtering is the "span" of a pattern. By "span" is meant the total number of places from the first symbol of a pattern to the last symbol of a pattern. Thus, the five symbol sequence illustrated in line 36 of the above example: P.SK.P . . . P (SEQ ID NO:7) has a span of seventeen (i.e., five symbols plus twelve placeholders).

This second selection criterion may be performed in several ways. Patterns may be selected by first reading the pattern symbols from the Pattern Map and then applying the selection criteria. Patterns either shorter than a predetermined first span, or longer than a second span may be selected or, patterns that meet both criteria may be selected. Patterns not meeting the criteria may then be deleted.

If there are more than two sequences the sequences are operated upon (e.g., as by concatenation) in pairs (in any order) until all possible pair-wise combinations have been operated upon and until all patterns have been identified. This set of patterns thus defines a set of "parent" patterns.

The present invention is also operative to detect patterns within a single sequence. In this instance the sequence is operated upon itself (as by concatenating it with itself).

Computational Complexity of Pattern Discovery

With large datasets the computational "cost" of a discovery method becomes important. A computationally efficient method may be able to use a desktop computer of modest performance rather than a high performance computer that may significantly increase the computational cost. An estimate of the order of magnitude of the computational cost of the basic method of the present invention follows. An estimate is made of each of the elemental steps of the method: the cost of computing the MOT tables; the cost of populating the Pattern Map; the cost of sorting the rows of the Pattern Map; and the cost of reading out the patterns from the Pattern Map. For the purposes of this complexity analysis it will be assumed that: (a) the population of each of the M alphabet symbols is approximately uniform; and (b) the symbols are randomly arranged in the sequences (this amounts to a limiting assumption of low sequence homology). The number of symbols is designated $N_1$ and $N_2$ in the two sequences. Further, it is also assumed that the two sequences are of roughly equal length, i.e., $N_1 \sim N_2 \sim N$.

1. Computing the MOT tables: The cost for each sequence is proportional to the number of symbols, so the total cost of computing the MOT tables is $N_1+N_2 \sim 2N$ 2. Populating the Pattern Map: It is necessary to form all possible combination of like symbols in each sequence. Since uniform symbol populations have been assumed, the number of occurrences of each symbol in sequence i is $N_i/M$. Therefore the cost of populating the Pattern Map is the product of the number of like symbols in each sequence, multiplied by the number of symbols, or $M(N_1/M * N_2/M) \sim (N_1 N_2/M) \sim N^2/M$.

3. Sorting the Pattern Map: Assume that the Pattern Map rows are uniformly populated. The average pattern length (number of symbols in each Pattern Map row) is $L_p \sim N_1 N_2 / [M(N_1+N_2)] \sim N/2M$.

Fast sorting algorithms, such as Quicksort (published by Sedgewick), run in time proportional to $L_p \log(L_p)$, so the sorting cost is $2N * N/2M * \log(N/2M) \sim N^2/M * \log(N/2M)$ since there are $(N_1+N_2) \sim 2N$ Pattern Map rows to be sorted.

4. Reading the patterns: This cost is identical to the cost of populating the Pattern Map.

Thus, the total cost is the sum of these components:

$2*N+N^2/M+(N^2/M)*\log(N/2M)$ or, keeping only the leading terms, $N^2/M*[2+\log(N/2M)]$.

Discovering Patterns Corrupted by
Insertions/Deletions

So far, a method has been described for discovering pure patterns between sequences. The patterns can be of arbitrary length and can be either separate, overlapped, or shared; however, they are still preserved exactly from one instance to the next.

The method of the present invention can be extended to discover "corrupted" patterns, where there may be one or more differences between one occurrence of the pattern and another. Generally, these differences take the form of insertions, where one or more additional symbols are added at locations within the pattern, and/or deletions, where one or more symbols are removed at locations within the pattern. This is believed to be a valuable addition since mutations which corrupt a sequence occur quite often in nature.

When discovering corrupted patterns the first steps of the method, viz., creating the two MOT tables, determining difference-in-position values, and created the Pattern Map, remain unchanged. When discovering pure patterns each row (or difference-in-position value) in the Pattern Map is treated separately and the entries in that row are sorted (in numerical order of index value) accordingly.

In generalizing the method to allow a maximum predetermined number C of insertions or deletions per location in the pattern, the Pattern Map is scanned from top to bottom and each C-adjacent rows in the Pattern Map are merged to create a new merged list. The entries in the resulting merged row are sorted by the position indices stored therein to create a merge-sorted list.

In the simplest case of allowing up to one insertion or deletion per pattern location (the value of C equals one) the Pattern Map is scanned and the entries in row one (i.e., position difference value of one) are combined with the entries in row two (i.e., position difference value of two) to create a merged row one. Merged row one may then be sorted to create the merge-sorted list.

Each (symbol, position index) pair in the merge-sorted list is converted to a (position index, total index, symbol) "triple", where the total index is defined by the sum of the position index and the row index. The order of the elements of the triple is immaterial.

From the merge-sorted list a "reference pattern" is read. The reference pattern is formed by placing symbols at relative locations given by the position indices in the merge-sorted list, with the caveat that only one instance of repeated position indices be read. The reason for this caveat is that when more than one row in the Pattern Map is merged it is possible for the same position index entry to be present more than once. When the combined row entries are then sorted it is possible to have identical, successive position indices in the merge-sorted list.

Having read the reference pattern all of the corrupted patterns can be read. This is done by using the total index, instead of the position index, to determine the relative locations of the symbols in the output corrupted pattern. In reading the corrupted patterns, where a position index repeats, there will be distinct instances of the total index. All possible combinations of the symbols are read, taking a single instance of the total index each time the position index repeats. Finally, recognizing that a single instance of the corrupted patterns will be identical to the reference pattern, that single corrupted pattern is included only once in the final output.

The entire process of merge-sorting adjacent rows in the Pattern Map and then creating a set of corrupted patterns is repeated (incrementing the starting row of the Pattern Map for each repeat) over the entire Pattern Map (stopping C rows before the end of the map). This process generates the entire family of corrupted patterns, where the maximum number of corruptions per pattern location is bounded by C.

However, a recursive method may be used. In the recursive method the value for C is initialized to one and all corrupted patterns are found. The value for C is incremented to two and all corrupted patterns are found. The value of C is incremented and the process is repeated until no more corrupted patterns are found.

The discovered patterns may be filtered using a predetermined selection criterion, as described in connection with FIG. 2.

A limit on the number of repetitions may also be imposed. For example, the number of repetitions may be limited to the cumulative number of symbol insertions and/or deletions permitted in a discovered corrupted pattern. This is important when the value of C is relatively large (e.g., three or more).

FIG. 3 illustrates the method of the present invention in discovering corrupted patterns. This figure shows two eleven-symbol sequences [DPUTPNQUNDT (SEQ ID NO:15) and DTUPPNOUNOT (SEQ ID NO:16 ) ] written in the alphabet D,N,O,P,T,U. The sequences are shown in sequence order and then repeated in symbol-sorted order to make clear the construction of the Pattern Map in the lower part of the FIG. 3. The Pattern Map is written somewhat more elaborately than in FIG. 2 in that each row of the Pattern Map is presented in the form of the (position index, total index, symbol) triple. The position index is exactly the index stored in the Pattern Map in FIG. 2. The total index is the sum of the position index and the Pattern Map row index (also known as the "difference in position" value). The symbol corresponds to the position index and is included in FIG. 3 primarily for clarity of explanation.

Consider rows thirteen and fourteen. These rows are merge-sorted to create list of Pattern Map entries of the form (symbol: position index, total index) thus:

(P:1,14),(P:1,15),(N:5,19),(O:6,20).

Notice that there are two instances containing a position index value of one, a first instance occurring at total index fourteen and the second instance at total index fifteen.

The reference pattern is simply described by the set of position indices (1,5,6) where the duplicate occurrence of the value one is ignored. This pattern is "P. . . NO" (SEQ ID NO:17).

The corrupted patterns can take two different forms depending on which instance of total index is chosen.

For the first form of the corrupted pattern the symbol "P" having the total index value of fourteen is selected (P:1, 14). The total indices of the symbols in the first form of corrupted pattern are thus (14,19,20) and the resulting pattern is "P . . . NO" (SEQ ID NO: 18), having an extra insertion between the P and N relative to the reference pattern ("P. . . NO") (SEQ ID NO: 17).

For the second form of the corrupted pattern the symbol "P" having the total index value of fifteen is selected (P:1,15). The total indices of the symbols in the second form of corrupted pattern are (15,19,20) and the resulting pattern is "P. . . NO" (SEQ ID NO: 17), which is identical to the reference pattern.

One corrupted pattern relative to the original reference pattern has thus been discovered. The occurrence of the reference pattern in the first sequence is DPUTP<u>N</u>OUNDT (SEQ ID NO: 15) and the occurrence of the reference pattern in the second sequence is DTUPPNOUNOT (SEQ ID NO: 16) (where the symbols of the pattern are underlined). By definition, the corrupted pattern may not be present in both sequences (otherwise it would have been discovered as a pure pattern). By examining the two sequences it may be seen that the corrupted pattern does not occur in the first sequence, but the corrupted pattern does occur as DTU<u>P</u>PNOU<u>NO</u>T (SEQ ID NO: 16) in the second sequence.

The number of corrupted patterns is the product of the number of times each position index occurs within the merge-sorted list. In the example the position index "one" occurs twice, the position index "five" occurs once and the position index "six" occurs once. Therefore, there are two corrupted patterns (2×1×1=2).

The computational cost of corrupted pattern discovery may be found, using a procedure similar to that, discussed above, for calculating the computational complexity of the sorting step. This results in a complexity factor of $(N_1 N_2 C/M) \log(N_1 N_2 C/NM)$ if $N_1, N_2 >> C$ If $N_1 \approx N_2 \sim N$, this reduces to $(N^2 C/M) \ln(NC/2M)$ and the total complexity of the discovery process is approximately $(N^2/M)(2+C \ln(NC/2M))$ which shares the same dependence on M.

In discovering corrupted patterns, multiple pairs of patterns which share a common first instance may be read from the merge-sorted list. This makes it difficult to estimate the total complexity of the final read stage. However, it is still safe to say that this complexity has the same dependence on N and M as indicated in the result above.

Increasing Pattern Support

The "support" of a pattern is defined as the number of sequences in which a pattern occurs. Patterns discovered by the method described heretofore have a support of at least two. The set of discovered parent patterns may be denoted as $^2P=\{^2P_1, ^2P_2, \ldots, ^2P_M\}$. The reason for the superscript "2" is that patterns discovered at this level have support $k \geq 2$. Sets of patterns that are guaranteed to have any given support k shall be denoted $^kP$, and shall be referred to as "k-patterns".

However, it is often the case that the "core" of a pattern is surrounded by "fringe noise", i.e., symbols which occur by chance rather than representing a biologically-significant signal. Fringe noise tends to lower the support of such patterns. Several methods may be used for discovering patterns having increased support, starting from the original set of discovered parent patterns.

Child Pattern Discovery

The "child pattern discovery" method relies on the fact that parent patterns discovered initially are represented in the same data structure (i.e., the MOT table) as the original sequences. Therefore, parent patterns may be used as a starting point for the methods described, instead of entire sequences. There are two implementations of child pattern discovery. In the first implementation parent patterns are paired with parent patterns. In the second implementation parent patterns are paired with original sequences. The advantage of the latter implementation is that there are many fewer sequences in a set of S sequences than there are parent patterns in $^2P$, requiring significantly reduced computation. Both implementations assume that the MOT tables used in the discovery of the parent patterns are still available.

Parent-Parent Child Pattern Discovery Implementation

A program written in pseudo-code for implementing Child Pattern Discovery from Parent-Parent pairs reads as follows:

```
Begin;
{
    For all [ ²Pᵢ, ²Pⱼ] in ²P;
    {
        Find MOTᵢ corresponding to ²Pᵢ, MOTⱼ corresponding to ²Pⱼ;
        Compute the Pattern Map of [MOTᵢ, MOTⱼ] ;
        Select a minimum number of symbols for output patterns;
            Read out patterns from the Pattern Map meeting the
                minimum number of symbols requirement,
                ignoring the rest;
            Store in MOT table form for further processing ;
            Cull duplicate patterns; }
}
End;
Parent-Sequence Child Pattern Discovery Implementation
    A program written in pseudo-code for implementing
Child Discovery from Parent-Parent pairs reads as
follows:
Begin;
{
    For all ²Pᵢ in ²P;
        For all Sⱼ in S;
        {
            Find MOTᵢ corresponding to ²Pᵢ, MOTⱼ
corresponding to Sⱼ;
```

-continued

```
            Compute the Pattern Map of [MOT_i, MOT_j];
            Select a minimum number of symbols for output
    patterns;
            Read out patterns from the Pattern Map meeting the
               minimum number of symbols requirement,
                  ignoring the rest;
               Store in MOT table form for further processing;
               Cull duplicate patterns;
            }
    }
End;
```

As another option, in either implementation of child pattern discovery "insignificant child" patterns may be culled. An "insignificant child" is defined as a child whose support is less than or equal to the support of its parents. Thus, sub-patterns that occur in the same locations in the same sequences will not be found. This avoids the discovery of redundant sub-patterns that carry less information.

Alternatives to Child Discovery

Sometimes it is impractical to perform child discovery due to the large numbers of patterns and sequences. Two alternative methods, termed "pattern trimming" and "pattern chopping", are available for finding sub-patterns that potentially have higher support.

Both "pattern trimming" and "pattern chopping" seek a set of sub-patterns from the set $^2P$ which are more "compact" on average than $^2P$. By "compact" it is meant the ratio of the number of symbols in a pattern divided by the span of the pattern. Patterns of higher compactness are more likely to have higher support and since patterns with fewer symbols are more likely to have higher support, no matter how the patterns are distributed spatially.

Figure 4:
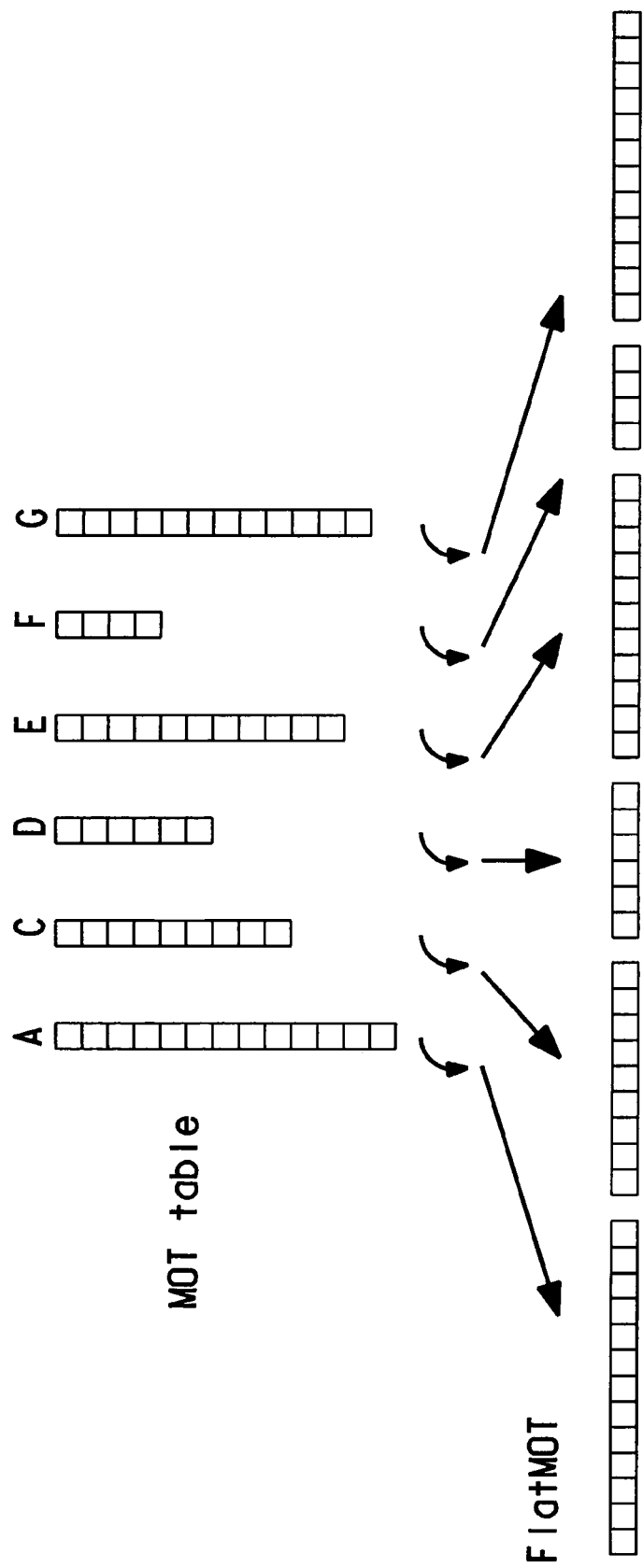
FIG. 4 illustrates a modified form of master offset table ("FlatMOT")

Both pattern trimming and pattern chopping methods rely on yet another data structure called the "FlatMOT" table, illustrated in FIG. 4. The FlatMOT table is closely related to the MOT table except that it has been "flattened" into a one-dimensional array of (symbol, index) ordered pairs. The FlatMOT table has the unique property that when sorted on symbol order it is similar to concatenating the columns of the MOT table into a one-dimensional array of indices, whereas when sorted on index order it is similar to the original sequence written as an array of symbols. The FlatMOT table is easily obtained directly from the MOT table, as suggested pictorially in FIG. 4.

As an example, the pattern

L.KV...V...PH (SEQ ID NO:4)

may be represented in FlatMOT table form as:

(L,0), (K,2), (V,3), (V,12), (P,21), (H,22).

The FlatMOT of the $i^{th}$ pattern may be denoted as $F_i$, and the $j_{th}$ ordered pair in $F_i$ as $F_i(j)$.

Figure 5:
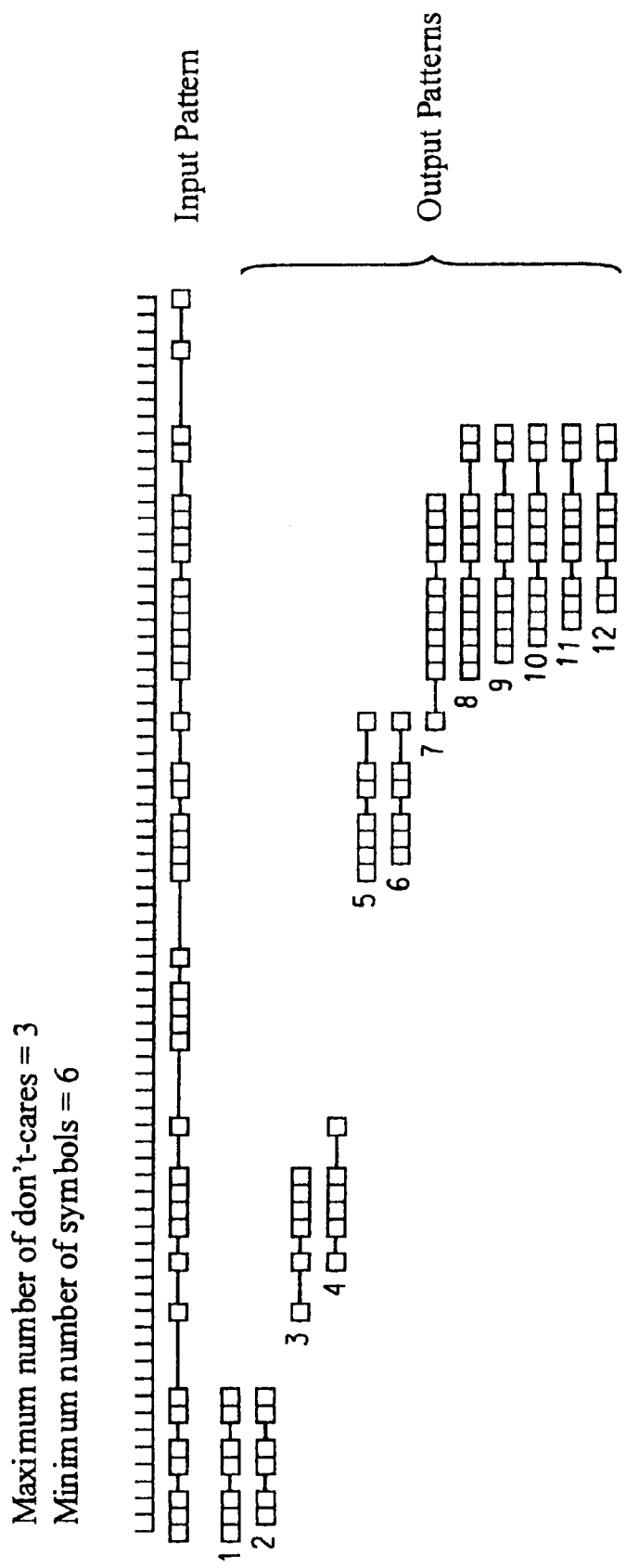
FIG. 5 shows the method of the present invention including a trimming step used to discover patterns of increased support.

Consider the sequence shown in FIG. 5 where the small squares represent locations where a symbol is present in the input pattern and the gaps between squares represent locations in the pattern where there is no symbol. A predetermined maximum allowable number "d" of placeholders (i.e., "don't-care" positions) in the pattern and a predetermined minimum number "n" of symbols for a candidate pattern are specified.

Trimming starts at the first symbol. From there, an interval is extended to the right, symbol-by-symbol, until the number of "don't-care" positions enclosed within the interval is greater than the given value "d" (d=3). If the number of symbols included in the interval is at least the minimum number "n" (n=6), then an output pattern indicted by the reference numeral "1" is created. In FIG. 5 the interval beginning at first place and ending at the ninth place of the input pattern and encompassing the first seven symbols of the input pattern satisfies these conditions. This interval contains three "don't-cares", two of which are embedded between symbols.

A second output pattern indicted by the reference numeral "2" satisfying the criteria begins at the second location of the input pattern and ends at the ninth location. The first and second output patterns both end at the same location due to the fact that the gap between seventh symbol (location nine) and the eighth symbol (location fourteen) of the input pattern exceeds the parameter d. Therefore, the next output pattern starts at the first symbol after this first large gap, i.e., at location fourteen.

A program written in pseudo-code for implementing pattern trimming is as follows:

```
Begin;
{
    Select d=maximum don't-cares, n=minimum number of
symbols
    For each F_i in ^2P;
    {
    For each symbol j in F_i;
        {
            Extend an interval to the right, accumulating
    enclosed don't cares,
                    until they exceed d;
                    If (number of symbols in the interval ≧ n)
    output as a pattern;
                    Else discard the pattern;
        }
    }
}
End;
```

Figure 6:
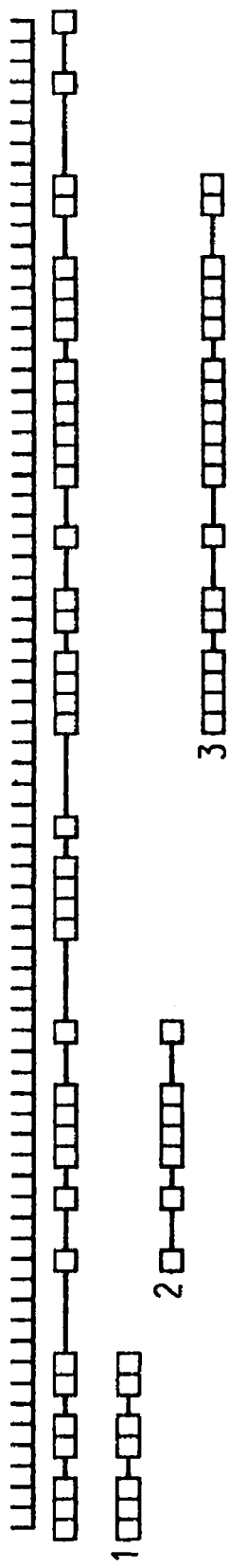
FIG. 6 shows the method of the present invention including a trimming step used to discover patterns of increased support.

FIG. 6 illustrates pattern chopping using the same input pattern as in FIG. 5. A predetermined maximum allowable number of contiguous placeholders between symbols in the pattern (a gap size g=3) and a predetermined minimum number of symbols for a candidate pattern (n=6) are specified. Chopping starts at the first symbol of the input pattern. An interval is extended to the right, symbol by symbol, until a first gap having a gap size g greater than three is found. This occurs between the seventh symbol (location nine) and eighth symbol (location fourteen) of the input pattern. This gap divides the input pattern into left and right segments. The left segment is tested to determine if it contains at least n (=6) symbols. Since the left segment contains seven symbols, the left segment becomes the output pattern indicted by the reference numeral "1".

The input pattern is replaced with the right segment, the eighth symbol (location fourteen) becomes the new starting point for chopping. An interval is extended to the right, symbol by symbol, until a second gap having a gap size g greater than three is found. The next gap that satisfies the gap size parameter is the gap between the fourteenth and fifteenth symbols of the original input pattern (locations twenty-five through thirty). This gap again divides the remainder of the input pattern into a left segment and a right segment. Since the number of symbols in the left segment exceeds the minimum criteria (n=6) it becomes the second output pattern, as indicted by the reference numeral "2".

The next gap that satisfies the gap size parameter is that gap between the nineteenth and twentieth symbols (locations thirty-five through forty). However, no output pattern is produced since the left segment defined by this gap contains only five symbols.

The method is repeated until the right segment contains too few symbols to meet the minimum symbol number criteria.

A program written in pseudo-code for implementing pattern chopping reads as follows:

```
Begin;
{
    Select g=critical gap size, n= minimum number of
symbols
    For each F_i in ²P;
    {
        Start at F_i (j=0);
        {
            Find first gap whose size is ≧ g;
            Divide F_i into a left piece and a right piece;
            If (left piece has at least n symbols) output
as a pattern;
            Else discard the pattern;
            Replace F_i with the right piece;
            Continue until length of right piece < n;
        }
    }
}
End;
```

As may be appreciated from the above discussion, pattern trimming can produce staggered, overlapping patterns since the starting point is moved through the parent pattern one symbol at a time. In contrast, pattern chopping produces non-overlapping patterns. Pattern chopping tends to be faster and more parsimonious, albeit at the risk of missing some patterns of interest that may be found by pattern trimming.

"Tuple" Discovery

"Tuple-Discovery" is an extension of the basic implementation of the present invention to more than two sequences. Tuple-Discovery completely discovers all patterns at all levels of support. Tuple-Discovery produces a plurality of Pattern Maps similar to that produced by the basic implementation of the present invention. Thereafter, however, it exploits information contained in these data structures more thoroughly by iteratively combining increasing numbers of sequences together and successively finding their common patterns.

Whereas the foregoing discussion of the present invention is couched in rather visual terms such as maps and tables, Tuple-Discovery is believed most conveniently described in algebraic terms. Therefore, a new notation is introduced for Pattern Maps based on k-tuples of sequence indices, where k is the level of support index as before. This notation and the underlying data structures may be envisioned as extensions of the aforementioned FlatMOT table (FIG. 4).

A k-tuple (or sometimes "tuple" for brevity) is written (l, m, n, ...) (for clarity, "l" here is the small alphabetic letter "L"). Each element in the k-tuple represents a sequence in a list of w-number input sequences.

A Master Offset Table is formed for each of the w sequences.

Each k-tuple has an associated tuple-table. The tuple-table represents, in index form, all of the patterns contained in the tuple. The tuple-table may be represented as an array of tuple-table entries. These are the elementary data structures of the tuple-table, and comprise a symbol and an array of difference-in-position values. By convention, difference-in-position values are taken with respect to the indices of the first (leftmost) sequence in the tuple. A tuple-table row entry is written $[S_{ix}:1_x, m_y, n_z, ...]$, where $S_{ix}$ is the symbol corresponding to the position index x in the $1^{th}$ sequence, and $m_y$ and $n_z$ are the difference-in-position values to all of the symbols in sequences m and n. The first index column in a tuple-table will be called the primary column for reasons that will become apparent.

A k-tuple table is thus formed of a plurality of columns, each column corresponding to one of the k sequences, comprising a first, primary, column and subsequent (k–1) suffix columns. The first, primary, column comprises the (symbol, position index) pairs of the first, primary, sequence. The subsequent (k–1) suffix columns comprise (symbol, difference-in-position value) pairs, where the differences in position value are the position differences between all possible like symbols of each remaining sequence of the tuple and the primary sequence of the tuple. The rows in the k-tuple table result from forming all possible combinations of like symbols from each sequence.

A sorted k-tuple table is then created by performing a multi-key sort on the k-tuple table. The sort keys are selected respectively from the difference-in-position value of the last suffix column ($k^{th}$ column) through the difference-in-position value of the first suffix column ($2^{nd}$ column).

A set of patterns common to the k sequences is defined by collecting adjacent rows of the sorted k-tuple table whose suffix columns contain identical sets of difference-in-position values, the relative positions of the symbols in each pattern being determined by the primary column position indices.

Variations on this particular method of representing a tuple-table may be made for purposes of either generality or speed. It shall be appreciated that any variation from the present method will share the essential characteristic of incrementally discovering patterns of increasing support among a set of input sequences.

Filtering methods described in conjunction with the basic implementation of the present invention may be employed. Thus patterns not meeting a predetermined criteria may be deleted. All patterns shorter than a first predetermined span and longer than a second predetermined span may be deleted. Alternatively all patterns having fewer than a predetermined number of symbols may be deleted.

Rows may be deleted from the k-tuple table according to predetermined criteria before reading out patterns. Rows may be deleted from the k-tuple table which do not have suffix indices identical to any other row of the k-tuple table. If $N_s$ is the minimum number of symbols per pattern, rows may be deleted from the k-tuple table if there are fewer than $N_s$ rows sharing identical suffix column difference-in-position values.

FIG. 7 illustrates an example of tuples and tuple-tables. The three sequences in the example are written in the alphabet {A,B,C,D}. The first course of tables are the 1-tuple tables. It should be appreciated that a 1-tuple is effectively the FlatMOT table of a single sequence. The transformation from a tuple-table to another may be described in terms of tuple operators.

The first operator, called "tuple-Extension", combines a k-tuple with a 1-tuple to form a (k+1)-tuple. Thus, tuple-Extension over a pair of one-tuples yields a two-tuple. The three possible two-tuples in this three-sequence problem are shown at the k=2 level.

The next operator is called "tuple-Sort". Note that the (0,1) tuple obtained by tuple-Extension is in alphabetic order. tuple-Sort converts this to index order. The order-of-sort key is from right-to-left in the tuple-table; that is, the rightmost column is the first sort key, followed by the next column to the left, and so forth.

The next operator is "tuple-Squeeze". This operator looks in the tuple-table for entries that have unique indices in all but the primary column, and deletes those entries. These entries correspond to single-symbol "-patterns". It is also possible to specify a criterion on the number of symbols required in a pattern greater to be than two. tuple-Squeeze readily generalizes to this case.

Figure 7A:
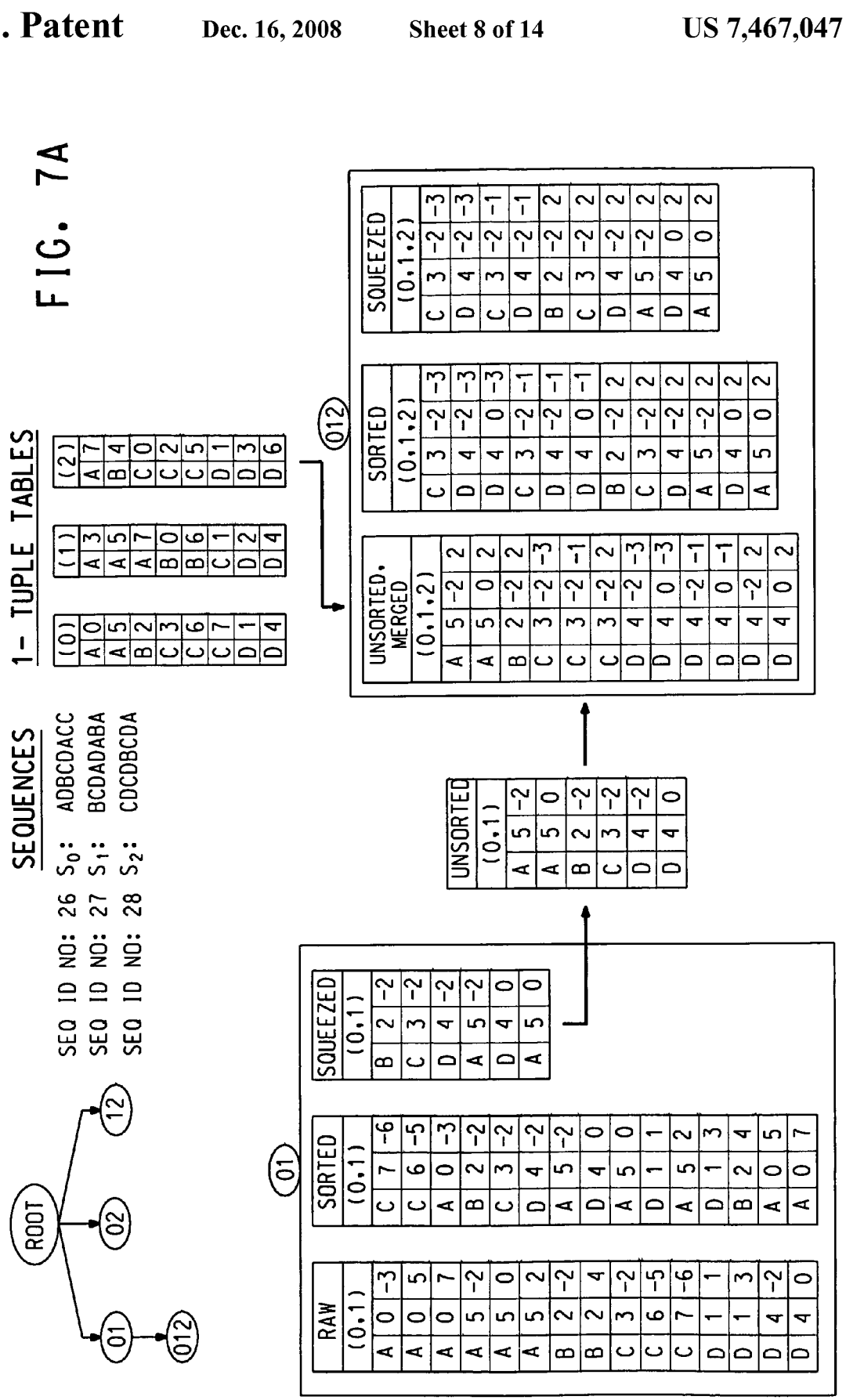
Figure 7B:
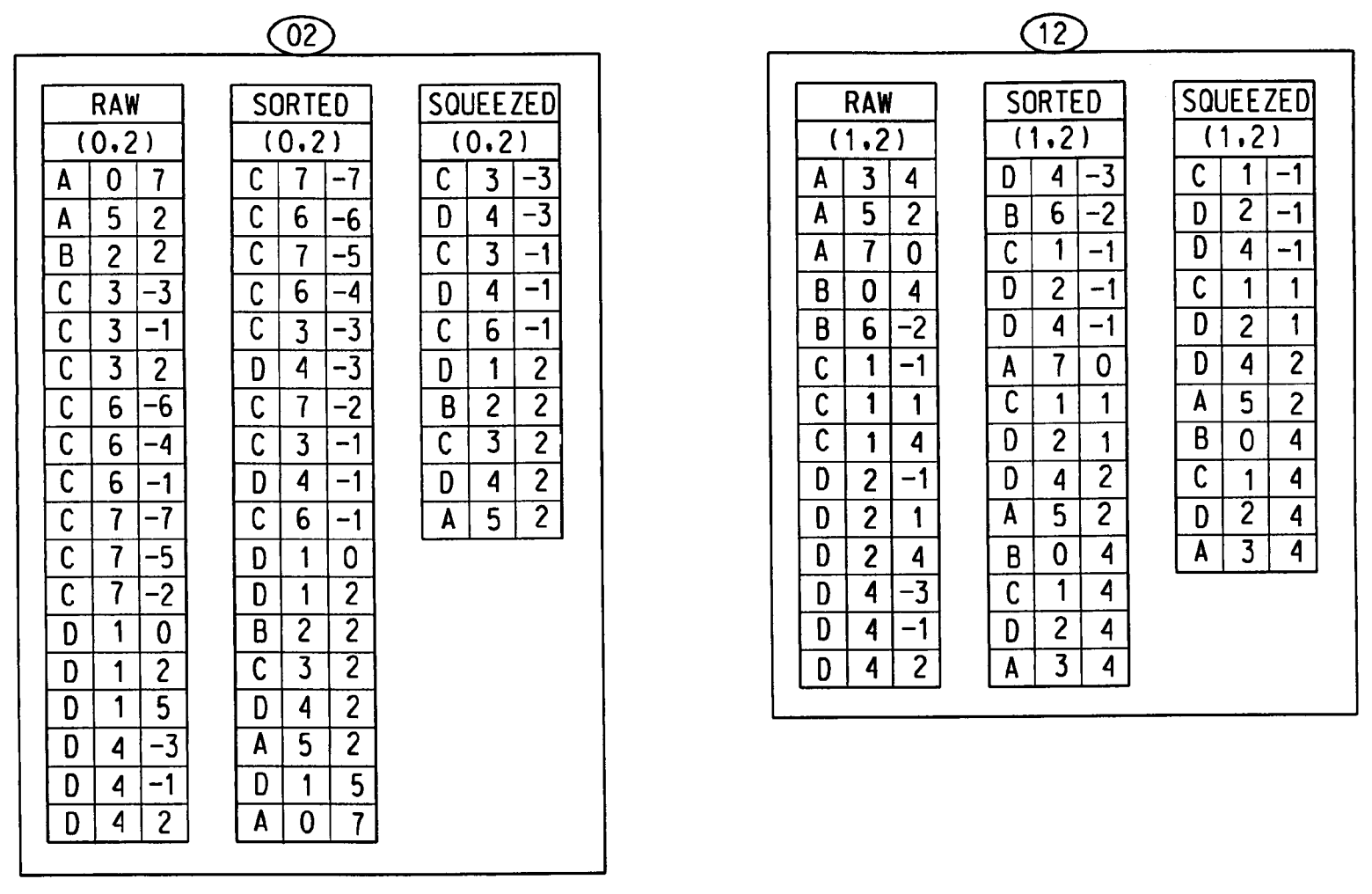

The result of tuple-Sort followed by tuple-Squeeze is shown in FIGS. 7A and 7B (labeled "squeezed"). All patterns contained in this tuple-table can be read. A pattern occurs as a contiguous set of tuple-table entries that share indices in all but the master column. Thus, for example, the first four rows of the (0,1) squeezed tuple-table read out as "BCDA" (SEQ ID NO: 19). The next two rows are the pattern "DA" (SEQ ID NO:20). The last two rows are "AD" (SEQ ID NO:2 1). These patterns are spaced according to the indices in the primary column. An example of a somewhat more distributed pattern can be seen in the (0,2) tuple-table, where the pattern "CD.C" (SEQ ID NO:22) is found. Note that the placeholder between the last two symbols of the pattern is due to the skip in the primary column from indices four to six.

Stated in other words, a (k+1)-tuple table may be formed by combining a k-tuple table with a sequence. To effect this a master offset table for the sequence is formed. Then, a (k+1)-tuple table of k+1 columns may be created by first forming all combinations of like symbols between the primary column of the k-tuple table and the master offset table, and then, for each such combination, duplicating the corresponding row of the k-tuple table, and appending a (symbol, difference-in-position value) pair corresponding to the difference between the position index of the master offset table and the position index of the primary column.

Patterns from a k-tuple table that are common to the k-tuple table and a (k+1)-tuple table may be deleted. This is accomplished by first deleting the suffix column corresponding to a sequence not shared between the two tuple-tables, thereby defining a modified table. Then rows from the k-tuple table whose suffix columns contain identical sets of difference-in-position values to a row of the modified table may be deleted.

The Tuple-tree

Tuple-Discovery comprises applying the tuple operators over all possible tuples that can be formed from a set of sequences. It is evident that this is a very large problem, since there are $(2^w-1)$ possible tuples given w sequences (including the one-tuples). For w=100 there are $\sim 10^{30}$ possible tuples. Thus, a practical solution requires finding which tuples need not be formed and visited.

Figure 8:
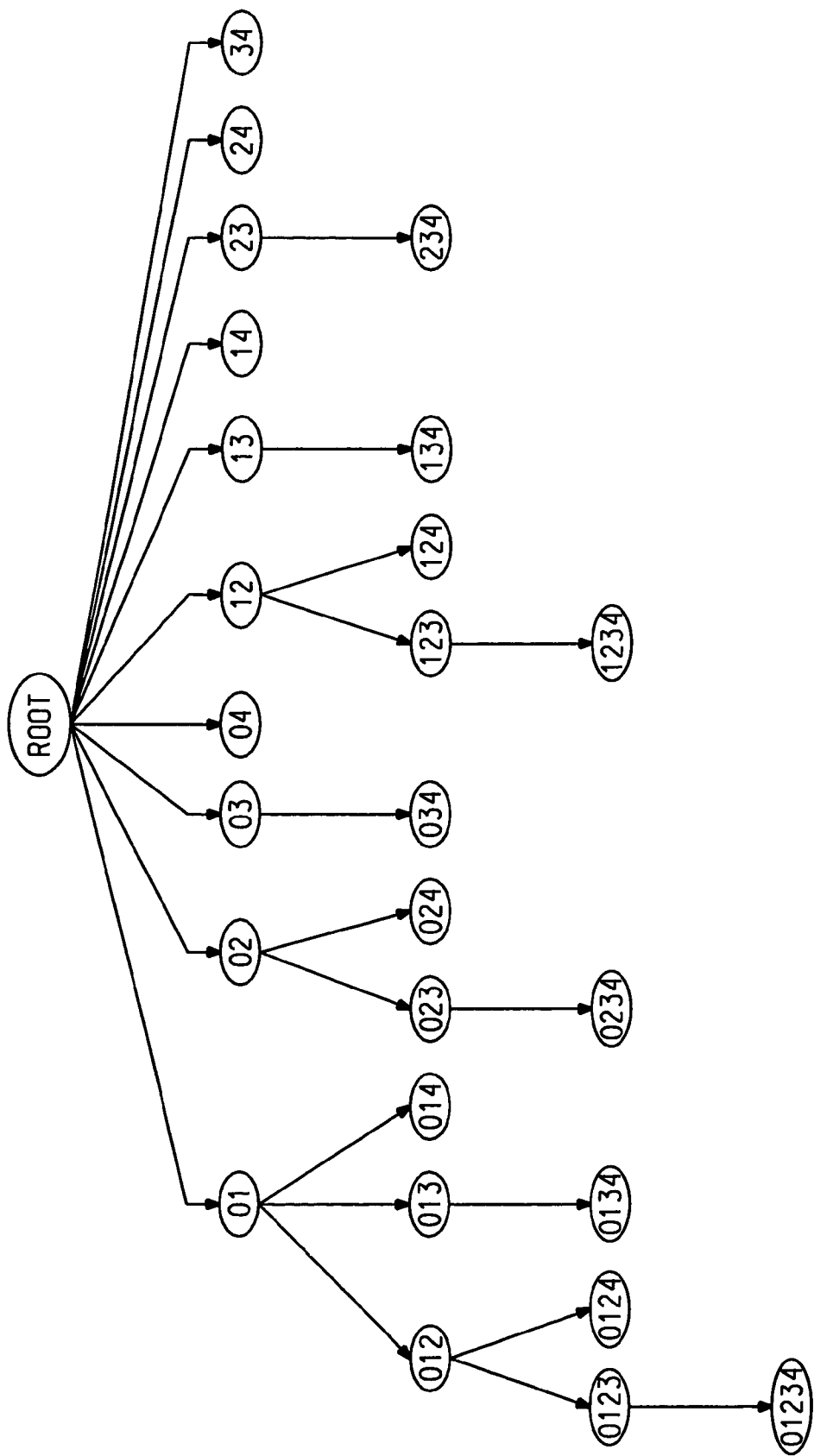
FIG. 8 shows a Pattern Map tree structure formed in accordance with the method of the present invention.

This problem can best be illustrated by creating a "tuple-tree" as shown in FIG. 8. From this tree it is evident that if any node is barren, that is, it fails to produce any patterns, then any node below it cannot produce patterns, and thus need not be visited. It should also be noted that due to the self-similar nature of k-tuples, the tuple-table never need be recalculated from scratch; it is always possible to derive a related tuple via an incremental calculation.

Figure 9:
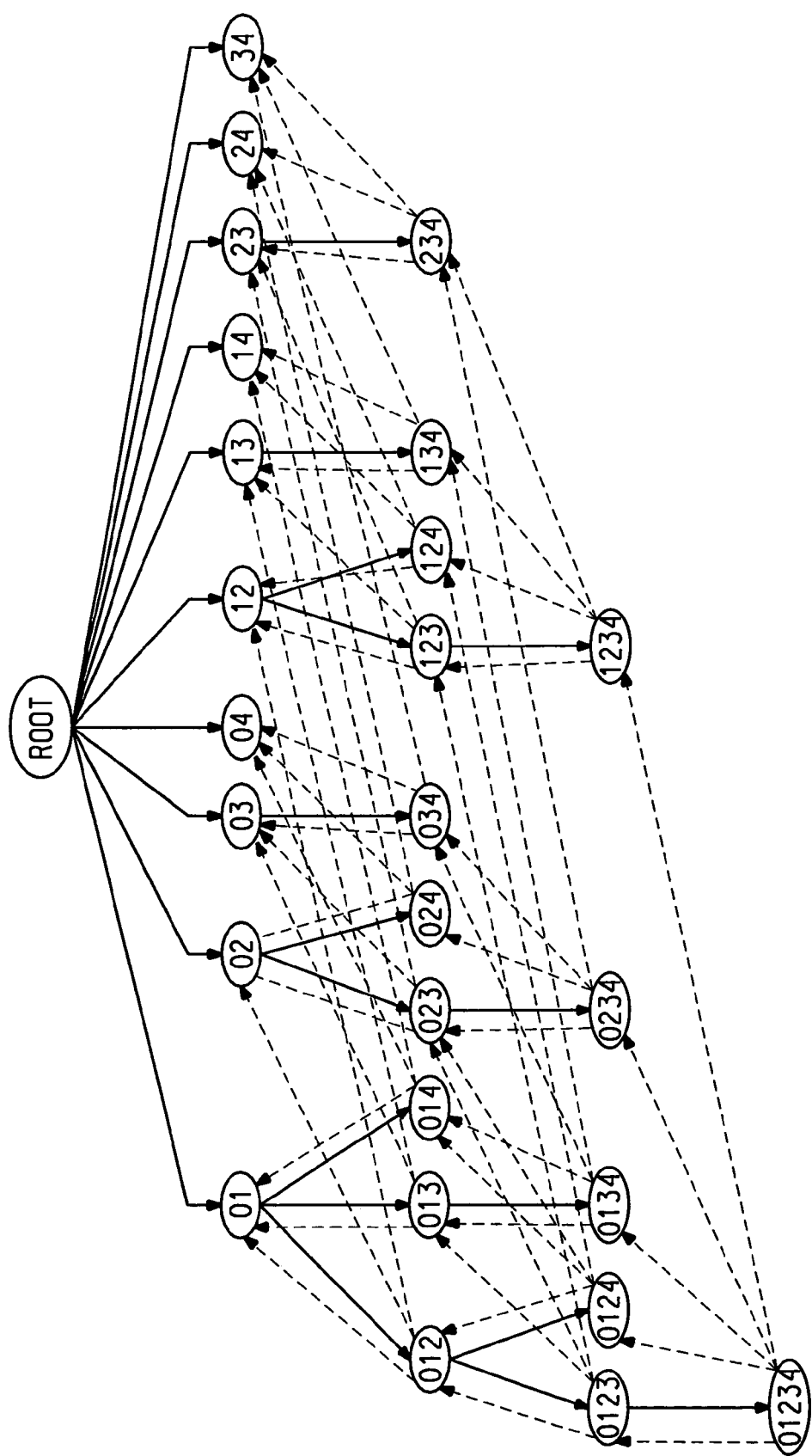
FIG. 9 shows all of the causal dependencies superimposed on the Pattern Map tree of FIG. 8.

Each node in FIG. 8 represents the k-tuple formed by the sequences indicated in the node. However, the corresponding tuple-tables are not all mutually independent since each sequence participates in forming multiple tuples. Thus there are causal relationships among nodes at adjacent k-levels. These causal dependencies point upwards; that is, the patterns implied by a particular (l,m,n,o) four-tuple must also be found (at least as sub-patterns) in the (l,m,n), (l,m,o), (l,n,o), and (m,n,o) three-tuples. FIG. 9 indicates with dotted arrows all of these causal dependencies superimposed on the tuple-tree.

This lack of independence of tuples may be exploited in a very important way. If it assumed that a particular pattern A is discovered in each of the three-tuples (l,m,n), (l,m,o), (l,n,o), and (m,n,o), it is unnecessary, and indeed undesirable, to report this pattern from any of these tuples. It is known that if the pattern exists on any two of these nodes it will also exist in the (l,m,n,o) four-tuple node. This illustrates the general principle that a pattern should be reported from only one tuple, namely the tuple of highest support in which it exists. Now it is possible to remove the duplicate pattern A from all three-tuples except the leftmost one, namely (l,m,n), knowing that from there the pattern will propagate to (l,m,n,o). This process is called "duplicate elimination", referring to duplicate patterns occurring at a given level of support.

An important consequence of duplicate elimination is that nodes to the right in the tuple-tree will in general die off sooner than they would otherwise. When a node dies its descendants are never visited, reducing the combinatorial complexity of the tuple-tree. Therefore, in addition to reducing the complexity of the output (that is, the total number of patterns) without loss of information, duplicate elimination has the additional benefit of reducing the computational complexity as a function of the size of the input (i.e. the number symbols in the sequences).

The embodiment described in FIGS. 8 and 9 makes use of linked lists of nodes in the tuple-tree, collecting together the nodes in a level of the tree. That is to say, all nodes at a given level of support are linked together in a doubly-linked list of nodes. This provides a means of accessing the nodes for the purposes of discovering, extending, reporting, and deleting. The list of nodes being processed is referred to as "parents" while the list being created (i.e. the children of the nodes on "parents") will be called "new_parents". Traversal of the tuple-tree is then accomplished by traversing each level in turn from left to right. Taking together the tuple data structure, the tuple operators, the organization of the tuples into a tree, and the elimination of duplicate patterns based on causal dependencies, a program in pseudo-code for implementing Tuple-Discovery is:

---

Tuple-Discovery pseudo-code, Version 1

```
Begin;
{
    parents = Initialize( );          /* form a list of
                          tuple-tree nodes corresponding to all
                              * 2-tuples, in sequence order, as
                          well as certain global
                              * data structures
                              */
    Foreach level, until no patterns are found, or the
    support of the level reaches the number of sequences
    in the input, process the list of nodes (parents) in
    that level
    {
        Foreach node in parents
        {
```

Tuple-Discovery pseudo-code, Version 1

```
        Foreach sequence[i] that can extend node
        {
              child = tupleExtend ( node, sequence [i] );
              child = tupleSort ( child );
              child = tupleSqueeze ( child );
              parents = MarkDuplicateElderPats ( child,
parents );
              add child to new_parents list;
        }
        report patterns on node;
        delete node;
      }
      parents = new_parents;
    }
  }
End;
```

Initialization produces a linked list of two-tuples, starting at node (0,1) and proceeding as follows: (0,1), (0,2), ..., (0,v), (1,2), ..., (1,v), ..., (v−1, v). Here, v is the maximum count in the list of sequences in the input, and is equal to the number w of input sequences less one, since by convention sequence count starts at zero. After initialization the nodes are processed in order of their appearance on the list of parents. For each node on the list the children (if any) are formed in turn. FIGS. 8 and 9 illustrates the fact that the indices of a child node of a parent node will be identical to the parent node, but with one additional index. The additional index is larger than the right-most index of the parent node.

The function "MarkDuplicateElderPats" visits each node in the parent list that is causally related to the current child, and marks as invalid any pattern it finds there that is duplicated in the current child. Any pattern thus marked invalid is neither reported nor propagated from that node. In this way duplicates are eliminated in the parent list prior to reading a node's patterns since the reading of a node's patterns is delayed until all of its children have been generated. Also, during the process of MarkDuplicateElderPats, if the parent's last pattern becomes invalid, the parent is deleted, and no others of its children are visited. This is a significant factor in eliminating the combinatorial complexity of the tuple-tree.

A pseudo-code program for implementing the operator MarkDuplicateElderPats is as follows:

MarkDuplicateElderPats Pseudo-code

```
Begin;
{
    Starting at current child's parent node, foreach
    node until the end of the list off parents
    {
         if the node is causally related to the current
child node
         {
              foreach pattern in the current child node
              {
                   foreach pattern in the node
                   {
                        if the node's pattern is equal to the
child's pattern, mark it invalid;
                   }
              }
         }
    }
}
End;
```

Significant performance improvements in Tuple-Discovery may be achieved by performing operations on a pattern-by-pattern basis rather than upon the tuple-table. Three significant changes over the first version of the Tuple-Discovery program hereinbefore described are:

1) the addition of the operator "PurifyLevel";
2) the substitution of the operator "MarkDuplicateParentPats" for "MarkDuplicateElderPats", and
3) the performance of operations called "patternExtend", "patternSort", and "patternSqueeze" on a pattern-by-pattern basis, rather than performing the operations tuple-Extend, tuple-Sort, and tuple-Squeeze on the entire Tuple-Table.

The performance improvements are due to the fact that, from a computational efficiency perspective, many small sort operations are faster than one large sorting operation. The improvement also explicitly recognizes the fact that patterns in a child always arise from one and only one pattern in the parent. Thus no generality is lost by breaking the parent up into discrete patterns for the purpose of applying the tuple operators.

A pseudo-code program for implementing a second version of the Tuple-Discovery method is as follows:

Tuple-Discovery pseudo-code, Version 2

```
Begin;
{
    parents = Initialize( );           /* form a list of
                                        Tuple-tree nodes corresponding to all
                                        * 2-tuples, in sequence order, as
                                        well as certain global
                                        * data structures
                                        */
    Foreach level, until no patterns are found, or the
    support of the level reaches the number of sequences
    in the input, process the list of nodes (parents) in
    that level
    {
         parents = PurifyLevel ( parents );
         Foreach node in parents
         {
              Foreach sequence [i] that can extend node
              {
                   create empty child node;
                   Foreach pattern in the parent node
                   {
                        tmp_pattern = patternExtend ( parent pattern,
sequence [i] );
                        tmp_pattern = patternSort ( tmp_pattern );
                        tmp_pattern = patternSqueeze ( tmp_pattern );
                        add tmp_pattern to child node;
                   }
                   parents = MarkDuplicateParentPats ( child,
parents );
                   add child node not empty, add it to
new_parents list;
              }
              report patterns on node;
              delete node;
         }
         parents = new_parents;
    }
}
End;
```

The operator PurifyLevel passes through the parents list, seeking and marking as invalid any duplicate patterns in that level. MarkDuplicateParentPats is similar to its predecessor with the exception that it no longer needs to visit any member of the parents list, except the parent of the child being processed, since PurifyLevel has already eliminated duplicate patterns in the parents list.

At this point additional notation is introduced. Patterns that should not propagate are designated (P') and patterns that should not report to the output are designated (R'), as opposed to the previous invalid patterns that neither propagated nor reported.

A pseudo-code program for implementing the operator PurifyLevel is as follows:

---
PurifyLevel pseudo-code for Tuple-Discovery Version 2
---
```
Begin;
{
    Foreach node in parents
    {
        Foreach pattern in node
        {
            Compare pattern with sequences, recording "hit list";
            Starting at the next node on parents, Foreach remaining node'
            {
                Check if node's indices match "hit list";
                if so, enter that node', search for duplicate of pattern;
                if found, mark it P', R', and mark pattern in node R';
            }
        }
    }
}
End;
```

The term "hit list" referred to immediately above is a list of sequences in which the pattern has been determined to occur. It is a list of integer indices where index value "0" indicates the first sequence in the input, "1" the second, and so forth. Each node in the tuple-tree is described by a set of k identifying indices, where k is the support of the node. In order for a node to match the hit list of a pattern all of its k identifying indices must match the hit list.

The essential feature of the operator PurifyLevel is that if one or more duplicates of a pattern are found all but the leftmost pattern are marked P'. Also note that none of these patterns are reported. This is because, as noted earlier, if a pattern is found on two or more nodes at a given level of support it will subsequently be found again at a higher level of support. Thus a pattern should not be reported until it is found at its ultimate level of support, and should be propagated from one and only one node, namely the leftmost node in which the pattern occurs.

Another improvement is the creation of a data structure termed "hash tree". Referring to the above pseudo-code program for PurifyLevel for Tuple-Discovery, Version 2, note that a list of nodes on the parent list is traversed, looking for those that match the hit list. This is computationally inefficient if the number of nodes on the parent list is large compared to the number that match the hit list. The hash tree allows construction of a node identity (list of integer sequence indices) from the hit list itself, and then, in k steps (where k is the level of support) determines if the node exists, and if so, then jumps directly to it.

Figure 10:
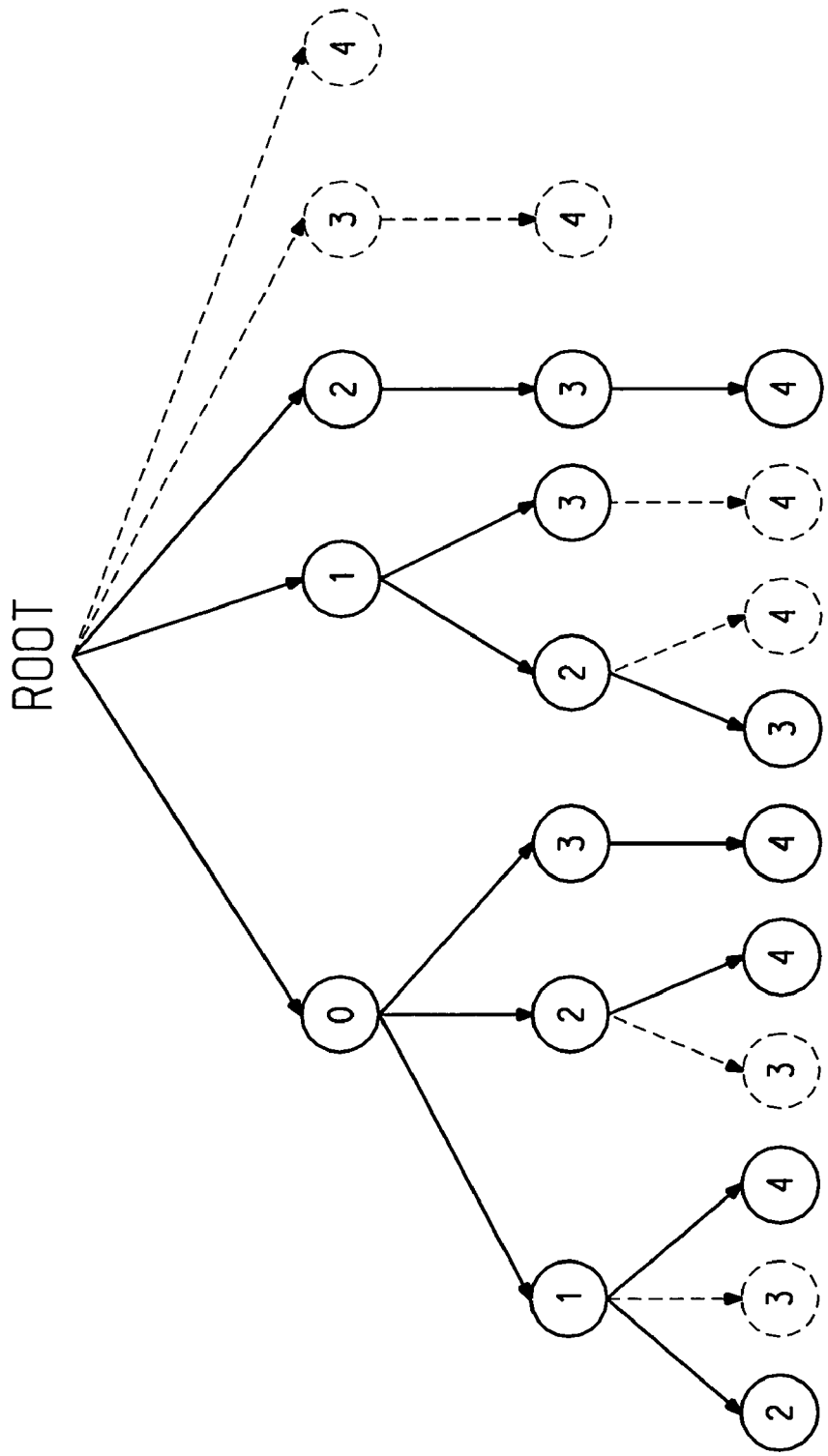
FIG. 10 shows the structure of a hash tree structure formed in accordance with the method of the present invention.

FIG. 10 is a pictorial representation of a hash tree corresponding to support level three for a set of five input sequences, labeled 0-4. Note that the number of levels in the hash tree equals the current level of support in the tuple-tree of FIG. 8. Null leaf nodes in the hash tree (shown dashed outline in FIG. 10) correspond to non-existent nodes in the tuple-tree. Non-null leaf nodes in the hash tree (shown in solid outline in FIG. 10) contain a pointer to the corresponding node in the tuple-tree and are added to the hash tree as the tuple-tree is built. The identifying indices of the corresponding tuple-tree node correspond to the path from the root of the hash tree. For example, the third non-null node from the left in the third level of FIG. 10 containing the digit "4" corresponds to tuple-tree node (0,2,4). The sequence numbers are read as the tree is traversed from the root. Thus, in order to arrive at the node in this example, the path passes through the node at the first level labeled "0", then through the node in the next level labeled "2", and finally to the leaf node in the third level "4". The content of this hash tree node is the address of tuple-tree node (0,2,4). Also note in FIG. 10 that there can be no support three-tuple that starts with index three or four, since with only five sequences in the set there is an insufficient number of sequences to construct these tuples. Thus, the corresponding hash tree nodes will be null by definition.

A pseudo-code program for implementing a third version of the Tuple-Discovery method is as follows:

---
Tuple-Discovery pseudo-code, Version 3
---
```
Begin;
{
    parents = Initialize( );            /* form a list of
                                         Tuple-tree nodes corresponding to all
                                         * 2-tuples, in sequence order, as
                                         well as certain global
                                         * data structures
                                         */
    Foreach level, until no patterns are found, or the
    support of the level reaches the number of sequences
    in the input, process the list of nodes (parents) in
    that level
    {
        Build Hash tree for current level
        parents = PurifyLevel ( parents );
        Foreach node in parents
        {
            Foreach sequence [i] that can extend node
            {
                create empty child node;
                Foreach pattern in the parent node
                {
                    tmp_pattern = patternExtend ( parent pattern, sequence [i] );
                    tmp_pattern = patternSort ( tmp_pattern );
                    tmp_pattern = patternSqueeze ( tmp_pattern );
                    add tmp_pattern to child node;
                }
                parents = MarkDuplicateParentPats ( child, parents );
                add child node not empty, add it to new_parents list;
            }
            report patterns on node
            delete node
        }
        parents = new_parents;
    }
}
End;
```

A program in pseudo-code for the operator PurifyLevel useful for Tuple-Discovery Version 3 is as follows:

PurifyLevel pseudo-code for Tuple-Discovery Version 3
```
Begin;
{
    Foreach node in parents
    {
        Foreach pattern in node
        {
            Compare pattern with sequences, recording "hit list";
```

Tuple-Discovery pseudo-code, Version 3

```
                Foreach k-combination of indices in hit list,
        search Hash tree for a non-null node'
                {
                        Search node' for duplicate of pattern;
                        if found, mark it P', R' in node', and mark
pattern in node R';
                }
        }
}
End;
```

A further modification to the Tuple-Discovery method is designated Tuple-Discovery Version 4. In this version two further changes are made. First, the manner in which duplicate patterns are handled is re-organized. Second, the tuples are organizing in a tree structure and the tree structure is traversed with the objective of visiting as few nodes as possible.

A pseudo-code program for implementing a fourth version of the Tuple-Discovery method is as follows:

Tuple-Discovery pseudo-code, Version 4

```
Begin;
{
        parents = Initialize( );          /* form a list of
tuple-tree nodes corresponding to all
        * 2-tuples, in sequence order, as well as certain
global
        * data structures
        */
        Foreach level, until no patterns are found, or the
support of the level reaches the number of sequences in
the input, process the list of nodes (parents) in that
level
        {
                Foreach node in parents
                {
                        Foreach sequence[i] that can extend node
                        {
                                create empty child node;
                                Foreach pattern in node
                                {
                                        Difference_table = NewPatternExtend (
pattern, sequence[I] );
                                        NewPatternSqueeze ( Difference_table,
child node );
                                }
                                if it is not empty, add child node to
new_parents list;
                        }
                        report all reportable patterns on parent node;
                        delete parent node;
                }
                parents = new_parents;
        }
}
End;
```

Two new operators are introduced in the pseudo-code of Version 4: "NewPatternExtend" and "NewPatternSqueeze". These operators are analogous to the operators tuple-Extend and tuple-Squeeze in the previous versions.

Figure 11A:
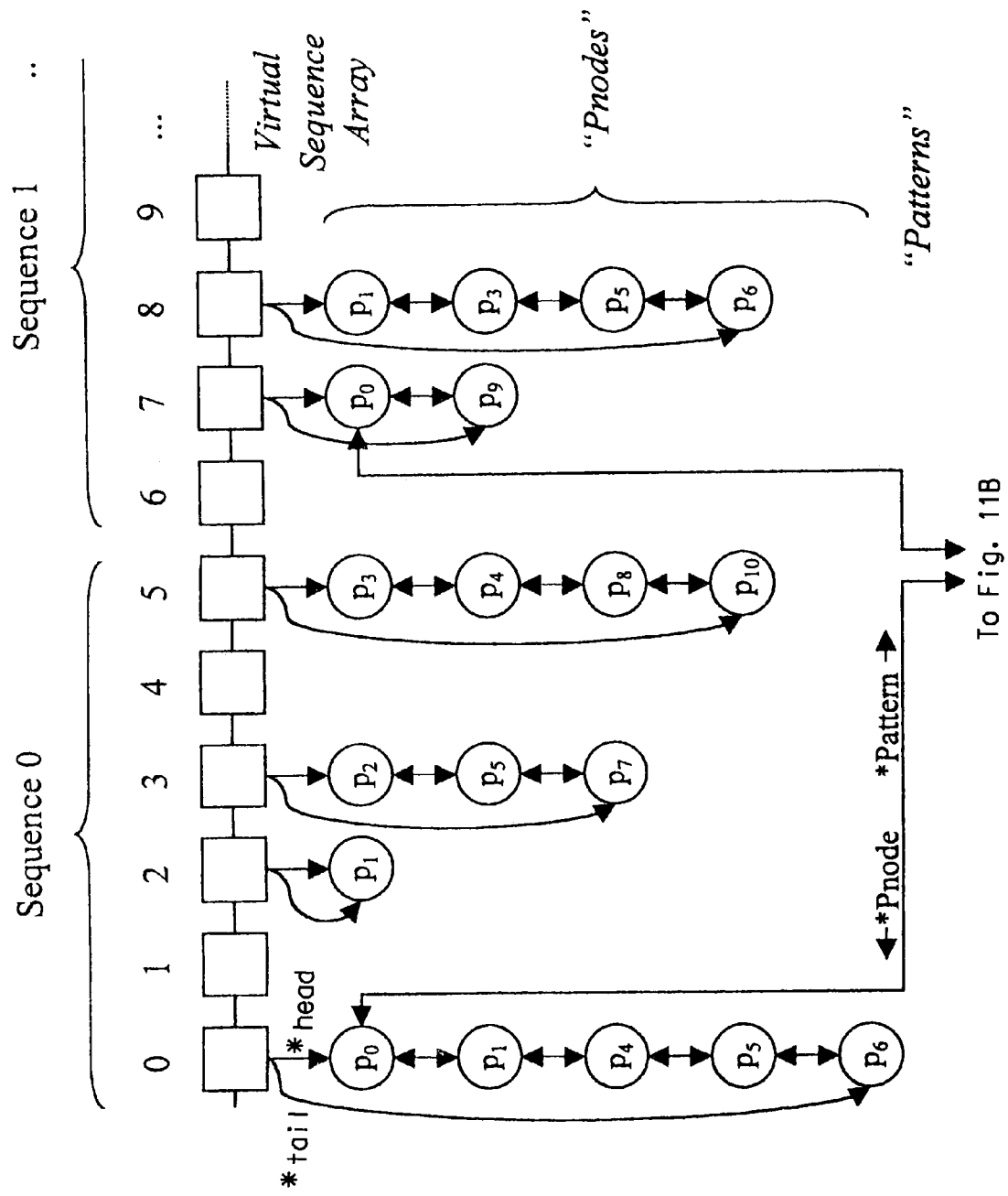
FIGS. 11A and 11B show a linked data structure formed in accordance with the method of the present invention.
Figure 11B:
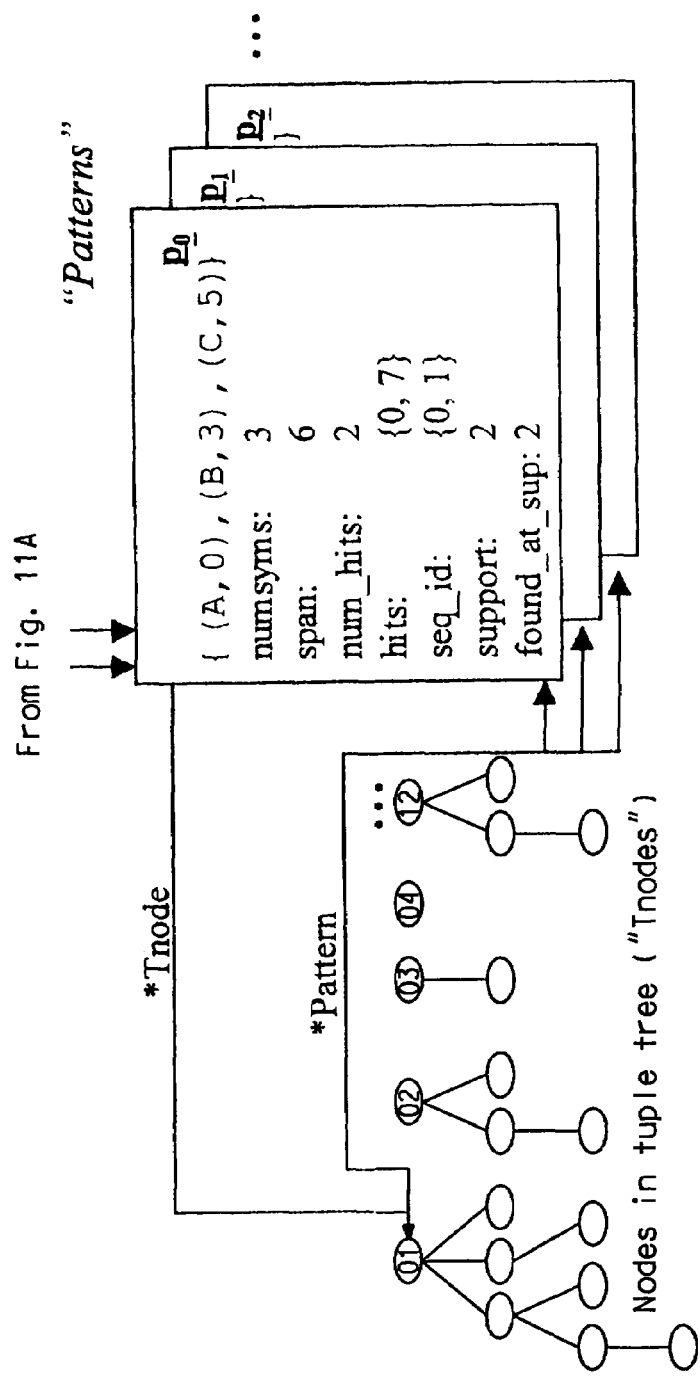

NewPatternExtend is similar to its predecessor operator except that it populates columns of a Pattern Map. The columns are subsequently parsed by the operator NewPatternSqueeze. NewPatternSqueeze passes through the Pattern Map looking for valid patterns. When it finds valid patterns it suppresses duplicate patterns and determines whether any remaining patterns are ready to be reported from the current node. It does so by means of the data structures depicted in FIG. 11.

A pseudo-code program for implementing the function NewPatternSqueeze is as follows:

NewPatternSqueeze pseudo-code - Tuple-Discovery Version 4

```
Begin;
{
        Foreach column in the Pattern Map
        {
                If ( number of symbols >= minimum number of
symbols &&
                        global density >= minimum global density &&
                        pattern meets local L,W density criterion )
                {
                        Find the P-node list corresponding the
pattern's occurrence in the tuple's
                                primary sequence;
                        Search the P-node list for a duplicate of the
pattern;
                        If a duplicate is found
                        {
                                If it was found at current level of support
                                {
                                        continue in loop;
                                }
                                Else
                                {
                                        Unlink the duplicate pattern from its old
T-node;
                                        Relink the pattern to the T-node
corresponding to the current child node;
                                }
                        }
                        Else
                        {
                                Add pattern to T-node corresponding to
current child node;
                                Find all locations of the pattern in the
Virtual Sequence Array;
                                Add a P-node for the pattern at each
location;
                        }
                }
        }
}
End;
```

The method, program and data structures of the present invention impart the capability to discover either pure or corrupted patterns from sequences, regardless of homology.

The program may be implemented using any suitable computing system, such as a desktop personal computer running under any popular operating such as Windows® 95 or later (Microsoft Corporation, Redmond, Wash.). Alternatively, a workstation such as that available from Sun MicroSystems, Inc., running under a Unix-based operating system may be used.

The program of instructions (typically written in C++ language) and data structures may be stored on any suitable computer readable medium, such as a magnetic storage medium (such as a "hard disc" or a "floppy disc"), an optical storage medium (such as a "CD-rom"), or semiconductor storage medium (such as static or dynamic RAM).

The capability to discover either pure or corrupted patterns from sequences makes possible structural and functional analyses such as pattern-based sequence clustering; motif discovery; and sequence/structure mapping.

Pattern-based sequence clustering is the co-occurrence of patterns which characterize functionally similar sequence groupings.

"Motifs" are patterns within a functional cluster that are coalesced into flexible expressions. Significant motifs are common to a functional cluster, and are unusual (or even non-existent) outside of the cluster. "Good" motifs are useful for finding novel, previously unknown, functional homologues, and for defining molecular targets for functional engineering.

Sequence/structure mapping is used to reveal structural similarity that will, in turn, reveal important functional similarity. Recurrent patterns may map out blocks of secondary protein structure. Assemblages of common secondary-structural themes reveal common fold families. Protein folding is perhaps the most important determinant of protein function.

Those skilled in the art, having the benefits of the teachings of the present invention as hereinabove set forth, may effect numerous modifications thereto. Such modifications are to be construed as lying within the contemplation of the present invention, as defined by the appended claims.

---

We claim:

1. A method of discovering one or more patterns in a set of k sequences of symbols, called a k-tuple, where k is greater than or equal to two, within an overall set of w sequences having sequence numbers 1, 2, . . . , w, the symbols being members of an alphabet, each sequence of symbols having respective lengths $L_1, L_2, \ldots, L_w$, comprising the steps of:
   a) translating the sequences of symbols into a table of ordered (symbol, position index) pairs, where the position index refers to the location of the symbol in a sequence;
   b) for each of the w sequences, grouping the (symbol, position index) pairs by symbol to form a respective master offset table, thus creating w master offset tables;
   c) using the position indices in the w master offset tables to determine the difference-in-position value between each occurrence of a symbol in one of the sequences and each occurrence of that same symbol in the other sequence in each master offset table, forming a k-tuple table associated with the k-tuple, the table comprising k columns, one of the k columns being a primary column and the remaining (k−1) columns being suffix columns, each column corresponding to one of the k sequences;
      i) the primary column comprising the (symbol, position index) pairs of a primary sequence,
      ii) the (k−1) suffix columns comprising (symbol, difference-in-position value) pairs, where the difference-in-position values are the position differences between all same symbols of each remaining sequence of the tuple and the primary sequence of the tuple,
      iii) the rows in the k-tuple table resulting from forming all combinations of same symbols from each sequence;
   d) creating a sorted k-tuple table by performing a multi-key sort on the k-tuple table, the sort keys being selected respectively from the difference-in-position values of the last suffix column ($k^{th}$ column) through the difference-in-position value of the first suffix column;
   e) identifying one or more patterns by collecting adjacent rows of the sorted k-tuple table whose suffix columns contain identical difference-in-position values, the relative positions of the symbols in each pattern being determined by the primary column position indices, the one or more patterns being common to the k sequences; and
   f) reading out the identified one or more patterns to a user.

2. The method of claim 1 further comprising:
   g) deleting all patterns not satisfying a predetermined criteria.

3. The method of claim 1 further comprising:
   g) deleting all patterns shorter than a first predetermined span and longer than a second predetermined span.

4. The method of claim 1 further comprising:
   g) deleting all patterns having fewer than a predetermined number of symbols.

5. The method of claim 1 further comprising the step of deleting rows from the k-tuple table according to predetermined criteria.

6. The method of claim 5, wherein rows sharing identical suffix column difference-in-position values are deleted from the k-tuple table if there are fewer than $N_s$ such rows, where $N_s$ is the minimum number of symbols per pattern.

7. The method of claim 1, further comprising the step of deleting rows from the k-tuple table which do not have suffix indices identical to any other row of the k-tuple table.

8. The method of claim 1, further comprising before step f), the step of finding all patterns at all levels of support within a set of sequences by:
   forming a tree of nodes, where each node corresponds to each combination of k sequences, and therefore represents a k-tuple, and wherein each node representing a k-tuple is connected to all nodes representing (k+1)-tuples,
   each (k+1)-tuple being formed by adding a unique sequence to the k-tuple, where the sequence being added is later in the ordered list of sequences than the latest sequence of the k-tuple;
   traversing the tree, and at each node visited during traversal, defining one or more patterns by collecting adjacent rows of the sorted k-tuple table whose suffix columns contain identical sets of difference-in-position values, the relative positions of the symbols in each pattern being determined by the primary column position indices, the one or more patterns being common to the k sequences.

9. The method of claim 8, wherein the traversal of the tree of nodes is accomplished via recursion.

10. The method of claim 8, further comprising the step of removing duplicate patterns at each level of support.

11. The method of claim 10, wherein the removal of duplicate patterns at each level of support is accomplished by:
   I) for each node corresponding to a (k+1)-tuple, identifying the nodes containing k-tuples whose sequences are subsets of the (k+1)-tuple; thereby defining a set of causally-dependent nodes;
   II) locating said causally-dependent nodes;
   III) removing from each said causally-dependent node the patterns in common with the (k+1)-tuple; and
   IV) if the k-tuple table in a causally-dependent node is thereby reduced to zero length, removing the corresponding node and all of its descendents from the tree prior to their traversal.

12. The method of claim 11, wherein locating causally-dependent nodes in step II) comprises the steps of:
   (A) organizing the nodes at level k in the Tuple-tree into a linked list which is ordered from left to right in accordance with the sequence numbers represented by each tuple; and
   (B) searching said linked list for nodes which are causally-dependent on a particular (k+1)-tuple.

13. The method of claim 11, wherein the nodes located in step II) are causally-dependent nodes at level k determined with respect to another node at level k, and are thus causally-dependent on a child of the another node at level k.

14. The method of claim 10, wherein the removal of duplicate patterns at each level of support comprises the steps of:
   I) organizing the nodes at level k in the Tuple-tree into a linked list which is ordered from left to right in accordance with the sequence numbers of each tuple;
   II) for each pattern in the current node at level k, storing a "hit list" array of the sequence numbers of the sequences containing the pattern;
   III) for all nodes to the right of the current node whose sequence numbers are all in the hit list, searching for a duplicate instance of the pattern, and if found, eliminating it; and
   IV) making each node the current node, repeating steps (II) and (III), in the order of the node's appearance in the linked list.

15. The method of claim 14, wherein, in step III), the nodes consistent with the hit list are found using a hash tree, the hash tree having a root and k levels of nodes, the k-th level of the hash tree having a plurality of leaf nodes, the respective level of nodes of the hash tree corresponding to the respective sequence numbers of a k-tuple, the leaf nodes identifying the k-tuple whose sequence numbers correspond to the path from the root to the leaf node, wherein searching the nodes for pattern duplicates is performed by repeating steps (II) and (III) for each node in the order of the appearance of that node in the hash tree.

16. The method of claim 8, wherein the traversing step itself comprises the steps of:
    i) creating a Virtual Sequence Array of patterns found within the sequences, wherein the patterns are termed P-nodes and the tuple nodes are termed T-nodes,
    (ii) finding a P-node list corresponding to the location of each pattern in the primary sequence of that tree node,
    iii) searching the P-node list for a duplicate instance of the pattern,
        (A) if no duplicate is found:
            (1) adding a pointer to the pattern of the current T-node pattern array,
            (2) finding all locations of the pattern within the Virtual Sequence Array,
            (3) adding a pointer to the pattern to each corresponding P-node array;
        (B) if a duplicate pattern is found:
            (1) ignoring the pattern if the duplicate pattern was found at support equal to the current level of support,
            (2) if the duplicate pattern was found at a previous level of support, unlinking the duplicate pattern from its previous T-node (if it exists), and relinking the duplicate pattern to the current T-node,
            (3) repeating steps 1) and 2) until all of the children of a T-node have been created, thus insuring that patterns of that T-node that are at their ultimate level of support are reported, and
            (4) deleting the T-node.

17. A method of discovering one or more patterns in a set of k+1 sequences of symbols, called a (k+1)-tuple, where k is greater than or equal to two, within an overall set of w sequences having sequence numbers $1, 2, \ldots, w$, the symbols being members of an alphabet, each sequence of symbols having respective lengths $L_1, L_2, \ldots, L_w$ by first forming a k-tuple table and then forming a (k+1)-tuple table by combining the k-tuple table with an additional sequence of symbols, the formation of the k-tuple table comprising the steps of:
    a) translating the sequences of symbols into a table of ordered (symbol, position index) pairs, where the position index refers to the location of the symbol in a sequence;
    b) for each of the w sequences, grouping the (symbol, position index) pairs by symbol to form a respective master offset table, thus creating w master offset tables;
    c) using the position indices in the w master offset tables to determine the difference-in-position value between each occurrence of a symbol in one of the sequences and each occurrence of that same symbol in the other sequence in each master offset table, forming a k-tuple table associated with the k-tuple, the table comprising k columns, one of the k columns being a primary column and the remaining (k−1) columns being suffix columns, each column corresponding to one of the k sequences;
        i) the primary column comprising the (symbol, position index) pairs of a primary sequence,
        ii) the (k−1) suffix columns comprising (symbol, difference-in-position value) pairs, where the difference-in-position values are the position differences between all same symbols of each remaining sequence of the tuple and the primary sequence of the tuple,
        iii) the rows in the k-tuple table resulting from forming all combinations of same symbols from each sequence;
    d) creating a sorted k-tuple table by performing a multi-key sort on the k-tuple table, the sort keys being selected respectively from the difference-in-position values of the last suffix column ($k^{th}$ column) through the difference-in-position value of the first suffix column;

the formation of the (k+1)-tuple table comprising the steps of:
    e) translating the additional sequence of symbols into a table of ordered (symbol, position index) pairs, where the position index refers to the location of the symbol in the additional sequence of symbols;
    f) grouping the (symbol, position index) pairs by symbol to form a master offset table;
    g) creating the (k+1)-tuple table of k+1 columns, one of the k+1 columns being a primary column and the remaining k columns being suffix columns, by:
        i) forming all combinations of same symbols between the primary column of the k-tuple table and the master offset table,
        ii) for each such combination, duplicating the corresponding row of the k-tuple table, and appending a (symbol, difference-in-position value) pair corresponding to the difference between the position index of the master offset table and the position index of the primary column;
    h) creating a sorted (k+1)-tuple table by performing a multi-key sort on the (k+1)-tuple table, the sort keys being selected respectively from the difference-in-position values of the last suffix column [$(k+1)^{th}$ column] through the difference-in-position value of the first suffix column;
    i) identifying one or more patterns by collecting adjacent rows of the sorted (k+1)-tuple table whose suffix columns contain identical difference-in-position values, the relative positions of the symbols in each pattern being determined by the primary column position indices, the one or more patterns being common to the k+1 sequences; and
    j) reading out the identified one or more patterns to a user.

18. The method of claim 17 further comprising the step of:
    k) deleting patterns from a k-tuple table common to the k-tuple table and a (k+1)-tuple table, where the (k+1)-tuple table contains all of the sequences of the k-tuple table with one additional sequence, by:
        i) deleting the suffix column corresponding to a sequence not shared between the two tuple tables, thereby defining a modified table, and
        ii) deleting all rows from the k-tuple table whose suffix columns all contain identical sets of difference-in-position values to a row of the modified table.

19. A method of discovering one or more patterns in a set of k sequences of symbols, called a k-tuple, comprising the steps of:
    a) for a first pair of sequences of the k-tuple
        i) translating each sequence of symbols into a table of ordered (symbol, position index) pairs, where the position index of each (symbol, position index) pair refers to the location of the symbol in the sequence;

ii) for each of the paired sequences, grouping the (symbol, position index) pairs by symbol to respectively form a first master offset table and a second master offset table;

iii) forming a Pattern Map comprising an array having (L1+L2−1) rows by:

A) subtracting the position index of the first master offset table from the position index of the second master offset table for every combination of (symbol, position index) pair having same symbols, the difference-in-position value resulting from each subtraction defining a row index;

B) storing each (symbol, position index) pair from the first master offset table in a row of the Pattern Map, the row being defined by the row index, until all (symbol, position index) pairs have been stored in the Pattern Map;

iv) identifying a parent pattern by collecting symbols having the identical difference-in-position value from each row of the Pattern Map and populating an output array with the collected symbols, the symbols being placed at relative locations in the parent pattern indicated by the position index of the (symbol, position index) pair; and v) repeating step iv) for each row of the Pattern Map;

b) storing the identified patterns as arrays of (symbol, position index) pairs;

c) for each subsequent pair of sequences of the k-tuple, replacing the (symbol, position index) pairs of the first sequence of the pair of sequences by the (symbol, position index) pairs of the stored patterns;

d) repeating steps (a) through (c) for each subsequent pair of sequences until the k-th sequence of the k-tuple is reached; and e) reading out the identified one or more patterns to a user.

20. A computer-readable medium containing a plurality of data structures useful in controlling a computer system to discover one or more patterns in k sequences of symbols within an overall set of w sequences, the plurality of data structures comprising:

a number w of master offset table data structures each grouping, for each value of a difference in position between each occurrence of a symbol in one of the sequences and each occurrence of that same symbol in each other sequence, the position (position index) in the first sequence of each symbol therein that appears in each of the other sequences at that difference-in-position value;

a k-tuple table data structure comprising columns and rows, the columns comprising (symbol, position index) pairs and (symbol, difference-in-position value) pairs; and a sorted k-tuple table data structure comprising a row-sorted representation of the (symbol, position index) pairs and (symbol, difference-in-position value) pairs contained in the k-tuple table data structure, wherein adjacent rows of the sorted k-tuple table data structure whose suffix columns contain identical difference-in-position values define one or more patterns of symbols, the relative positions of symbols in each pattern being determined by the primary column position indices in the sorted k-tuple table data structure.

21. The computer-readable medium of claim 20 wherein the sorted k-tuple table data structure further groups, for each value of a difference in position, the number of symbols in the first sequence that appear in the second sequence at that difference-in-position value.

22. A computer-readable medium containing instructions for controlling a computer system to discover one or more patterns in a set of k sequences of symbols, called a k-tuple, where k is greater than or equal to two, within an overall set of w sequences having sequence numbers 1, 2, . . . , w , the symbols being members of an alphabet, each sequence of symbols having respective lengths $L_1, L_2, \ldots, L_w$, by executing a method comprising the steps of:

a) translating the sequences of symbols into a table of ordered (symbol, position index) pairs, where the position index refers to the location of the symbol in a sequence;

b) for each of the w sequences, grouping the (symbol, position index) pairs by symbol to form a respective master offset table, thus creating w master offset tables;

c) using the position indices in the w master offset tables to determine the difference-in-position value between each occurrence of a symbol in one of the sequences and each occurrence of that same symbol in the other sequence in each master offset table, forming a k-tuple table associated with the k-tuple, the table comprising k columns, one of the k columns being a primary column and the remaining (k−1) columns being suffix columns, each column corresponding to one of the k sequences;

i) the primary column comprising the (symbol, position index) pairs of a primary sequence, ii) the (k−1) suffix columns comprising (symbol, difference-in-position value) pairs, where the difference-in-position values are the position differences between all same symbols of each remaining sequence of the tuple and the primary sequence of the tuple, iii) the rows in the k-tuple table resulting from forming all combinations of same symbols from each sequence;

d) creating a sorted k-tuple table by performing a multi-key sort on the k-tuple table, the sort keys being selected respectively from the difference-in-position values of the last suffix column ($k^{th}$ column) through the difference-in-position value of the first suffix column;

e) identifying a one or more patterns by collecting adjacent rows of the sorted k-tuple table whose suffix columns contain identical difference-in-position values, the relative positions of the symbols in each pattern being determined by the primary column position indices, the one or more patterns being common to the k sequences; and f) reading out the identified one or more patterns to a user

* * * * *

SEQUENCE LISTING

```
<160> NUMBER OF SEQ ID NOS: 2

<210> SEQ ID NO 1
<211> LENGTH: 47
<212> TYPE: PRT
<213> ORGANISM: Artificial Sequence
<220> FEATURE:
<223> OTHER INFORMATION: Sequence of Symbols S1
<220> FEATURE:
<221> NAME/KEY: MISC_FEATURE
<222> LOCATION: (1)..(47)
<223> OTHER INFORMATION:

<400> SEQUENCE: 1

Glu Cys Gly His His Ala Phe Ser Asp Tyr Gln Trp Val Asp Asp Glu
1               5                   10                  15

Asn Pro Leu Gln Lys Val Pro Thr Ser Lys Pro Pro Phe Thr Val Gly
            20                  25                  30

Asp Ile Lys Lys Ala Ile Pro Pro His Cys Phe Gln Arg Ser Leu
        35                  40                  45

<210> SEQ ID NO 2
<211> LENGTH: 54
<212> TYPE: PRT
<213> ORGANISM: Artificial Sequence
<220> FEATURE:
<223> OTHER INFORMATION: Sequence of Symbols S2
<220> FEATURE:
<221> NAME/KEY: MISC_FEATURE
<222> LOCATION: (1)..(52)
<223> OTHER INFORMATION:

<400> SEQUENCE: 2

Cys Glu Val Gly Val Val Leu Arg Lys Val Lys Pro Val Ser Lys Val
1               5                   10                  15

Pro Ile Val Phe Gln Arg Ser Leu Val Pro Thr Pro His Val Leu Arg
            20                  25                  30

Lys Ala Trp Val Cys Val Tyr Glu Ala Gly His His Gln Tyr Trp Phe
        35                  40                  45

Tyr Gly Trp Val Asn Gly
    50
```